US008529927B2

(12) United States Patent
Chang et al.

(10) Patent No.: US 8,529,927 B2
(45) Date of Patent: Sep. 10, 2013

(54) ALPHA-2 AGONIST POLYMERIC DRUG DELIVERY SYSTEMS

(75) Inventors: James N. Chang, Newport Beach, CA (US); Lon T. Spada, Walnut, CA (US); Wendy M. Blanda, Tustin, CA (US); Werhner C. Orilla, Anaheim, CA (US); James A. Burke, Santa Ana, CA (US); Patrick M. Hughes, Aliso Viejo, CA (US)

(73) Assignee: Allergan, Inc., Irvine, CA (US)

( * ) Notice: Subject to any disclaimer, the term of this patent is extended or adjusted under 35 U.S.C. 154(b) by 853 days.

(21) Appl. No.: 11/394,765

(22) Filed: Mar. 31, 2006

(65) Prior Publication Data

US 2006/0233860 A1 Oct. 19, 2006

Related U.S. Application Data

(63) Continuation-in-part of application No. 11/119,021, filed on Apr. 29, 2005, which is a continuation-in-part of application No. 10/836,911, filed on Apr. 30, 2004.

(51) Int. Cl.
| | | |
|---|---|---|
| *A61K 9/00* | (2006.01) | |
| *A61K 31/415* | (2006.01) | |
| *A61K 31/417* | (2006.01) | |
| *A61K 31/498* | (2006.01) | |
| *A01N 43/50* | (2006.01) | |

(52) U.S. Cl.
USPC ........ 424/422; 424/427; 424/428; 514/234.8; 514/401; 514/402; 514/912; 514/913; 514/953; 514/954; 514/955; 544/383

(58) Field of Classification Search
None
See application file for complete search history.

(56) References Cited

U.S. PATENT DOCUMENTS

| | | | | |
|---|---|---|---|---|
| 4,327,725 A | 5/1982 | Cortese et al. | ............... | 128/260 |
| 4,474,451 A | 10/1984 | Mizokami | ............... | 354/418 |
| 4,521,210 A | 6/1985 | Wong | ............... | 604/8 |
| 4,853,224 A | 8/1989 | Wong | ............... | 424/427 |
| 4,997,652 A | 3/1991 | Wong | ............... | 424/428 |
| 5,164,188 A * | 11/1992 | Wong | ............... | 424/428 |
| 5,443,505 A | 8/1995 | Wong et al. | ............... | 623/6 |
| 5,501,856 A | 3/1996 | Ohtori et al. | ............... | 424/428 |
| 5,632,984 A * | 5/1997 | Wong et al. | ............... | 424/85.4 |
| 5,766,242 A | 6/1998 | Wong et al. | ............... | 623/66 |
| 5,824,072 A | 10/1998 | Wong | ............... | 623/6 |
| 5,856,329 A | 1/1999 | Wheeler et al. | ............... | 514/255 |
| 5,869,079 A | 2/1999 | Wong et al. | | |
| 6,074,661 A | 6/2000 | Olejnik et al. | ............... | 424/427 |
| 6,194,415 B1 | 2/2001 | Wheeler et al. | ............... | 514/252.1 |
| 6,248,741 B1 | 6/2001 | Wheeler et al. | ............... | 514/249 |
| 6,309,669 B1 * | 10/2001 | Setterstrom et al. | ............... | 424/486 |
| 6,331,313 B1 | 12/2001 | Wong et al. | ............... | 424/427 |
| 6,369,116 B1 | 4/2002 | Wong et al. | ............... | 424/484 |
| 6,410,045 B1 * | 6/2002 | Schultz et al. | ............... | 424/429 |
| 6,447,796 B1 * | 9/2002 | Vook et al. | ............... | 424/422 |
| 6,465,464 B2 | 10/2002 | Wheeler et al. | ............... | 514/249 |
| 6,699,493 B2 | 3/2004 | Wong | ............... | 424/426 |
| 7,589,057 B2 | 9/2009 | Chang et al. | | |
| 8,293,741 B2 | 10/2012 | Burke et al. | | |
| 2002/0032201 A1 * | 3/2002 | Olejnik et al. | ............... | 514/249 |
| 2002/0094998 A1 * | 7/2002 | Burke et al. | ............... | 514/396 |
| 2003/0157178 A1 * | 8/2003 | Chen et al. | ............... | 424/486 |
| 2004/0054374 A1 | 3/2004 | Weber et al. | ............... | 606/107 |
| 2004/0151753 A1 | 8/2004 | Chen et al. | | |
| 2004/0208910 A1 * | 10/2004 | Ashton et al. | ............... | 424/427 |
| 2005/0154399 A1 | 7/2005 | Weber et al. | ............... | 606/107 |
| 2005/0244458 A1 * | 11/2005 | Huang et al. | ............... | 424/426 |
| 2005/0244463 A1 | 11/2005 | Huang et al. | | |
| 2005/0244476 A1 | 11/2005 | Burke et al. | | |
| 2005/0244479 A1 | 11/2005 | Huang et al. | | |
| 2005/0244506 A1 | 11/2005 | Burke et al. | | |
| 2008/0118547 A1 | 5/2008 | Huang et al. | | |
| 2008/0118548 A1 | 5/2008 | Huang et al. | | |
| 2008/0118549 A1 | 5/2008 | Huang et al. | | |
| 2008/0131372 A1 | 6/2008 | Huang et al. | | |
| 2008/0131485 A1 | 6/2008 | Huang et al. | | |

(Continued)

FOREIGN PATENT DOCUMENTS

| | | |
|---|---|---|
| EP | 0 992 244 | 4/2000 |
| WO | WO 02/02076 | 1/2002 |

(Continued)

OTHER PUBLICATIONS

JL Cleland, ET Duenas, A Park, A Daugherty, J Kahn, J Kowalski, A Cuthbertson. Development of poly-(D,L-lactidecoglycolide) microsphere formulations containing recombinant human vascular endothelial growth factor to promote local angiogenesis. Journal of Controlled Release 72 (2001) 13-24.*

LA Wheeler, DW Gil, E WoldeMussie. Role of Alpha-2 Adrenergic Receptors in Neuroprotection and Glaucoma. Survey of Ophthalmology vol. 45 Supplement 3, May 2001. S290-S294.*

B Conti, C Bucolo, C Giannavola, G Puglisi, p. Giunchedi, U Conte. "Biodegradable microspheres for the intravitreal administration of acyclovir: in vitro / in vivo evaluation." European Journal of Pharmaceutical Sciences, vol. 5, 1997, pp. 287-293.*

Sigma-Aldrich. Biodegradable Polymers. http://www.sigmaaldrich.com/materials-science/polymer-science/resomer.printerview.html. Accessed May 25, 2011. 3 printed pages.*

(Continued)

Primary Examiner — Frederick Krass
Assistant Examiner — Isaac Shomer
(74) Attorney, Agent, or Firm — Laura L. Wine; Joel B. German; Debra D. Condino

(57) ABSTRACT

Biocompatible intraocular implants include an alpha-2 adrenergic receptor agonist and a polymer associated with the alpha-2 adrenergic receptor agonist to facilitate release of the alpha-2 adrenergic receptor agonist into an eye for an extended period of time. The alpha-2 adrenergic receptor agonist may be associated with a biodegradable polymer matrix, such as a matrix of a two biodegradable polymers. The implants can be placed in an eye to treat one or more ocular conditions, such as an ocular vasculopathy or glaucoma, including reduction of an elevated intraocular pressure.

4 Claims, 15 Drawing Sheets

(56) References Cited

U.S. PATENT DOCUMENTS

| | | |
|---|---|---|
| 2008/0260832 A1 | 10/2008 | Burke et al. |
| 2008/0299178 A1 | 12/2008 | Burke et al. |
| 2011/0251201 A1 | 10/2011 | Huang et al. |

FOREIGN PATENT DOCUMENTS

| | | |
|---|---|---|
| WO | WO 02/36162 | 5/2002 |
| WO | WO 02/43785 | 6/2002 |
| WO | WO 03/077952 | 9/2003 |
| WO | WO 2004/669979 | 8/2004 |

OTHER PUBLICATIONS

CAS Registry Record from 59803-98-4 (Brimonidine). Entered STN Nov. 16, 1984. 1 page.*

Heller, Biodegradable Polymers in Controlled Drug Delivery, In: CRC Critical Reviews in Therapeutic Drug Carrier Systems, vol. 1, CRC Press, Boca Raton, FL 1987, pp. 39-90.

USP 23; NF 18 (1995) pp. 1790-1798.

Gao, Hua., et al., *Up-regulation of Brain-Derived Neurotrophic Factor Expression by Brimonidine in Rat Retinalo Ganglion Cells*, Arch Ophthalmol Jun. 2002 120(6), pp. 797-803.

http://macular-degeneration.emedtv.com/macular-degeneration/macular-degeneration-genetics.html, Oct. 31, 2006.

Merkli et al, "Use of Insoluble Biodegradable Polymers in Ophthalmic Systems for the Sustained Release of Drugs", European Journal of Pharmaceutics and Biopharmceutics, pp. 271-283; Oct. 1, 1995.

USPTO BPAI Decision on Appeal No. 2010-004999 in U.S. Appl. No. 10/836,911, mailed Oct. 25, 2010.

U.S. Appl. No. 11/119,021, filed Apr. 29, 2005.

U.S. Appl. No. 11/395,019, filed Mar. 31, 2006.

* cited by examiner

Figure 18. Implant Release Profiles
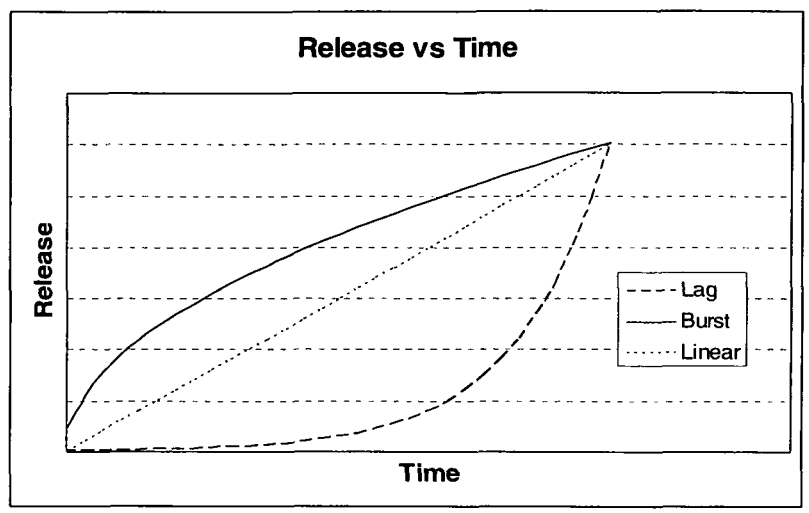

Figure 19. Short term in vitro Release Profile of the Table 4 Implants
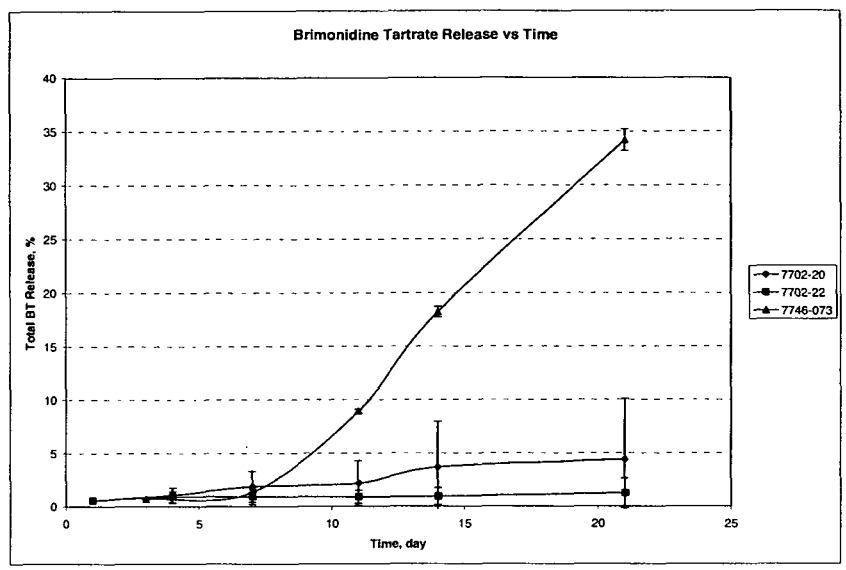
Figure 20. Long-Term in vitro Release Profile of the Table 4 Implants
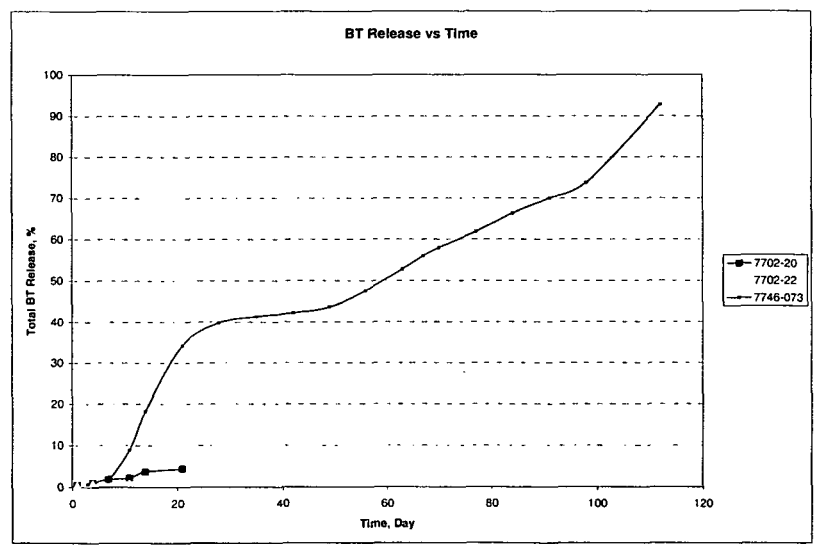

Figure 21. Short term in vitro Release Profile of the Table 5 Implants
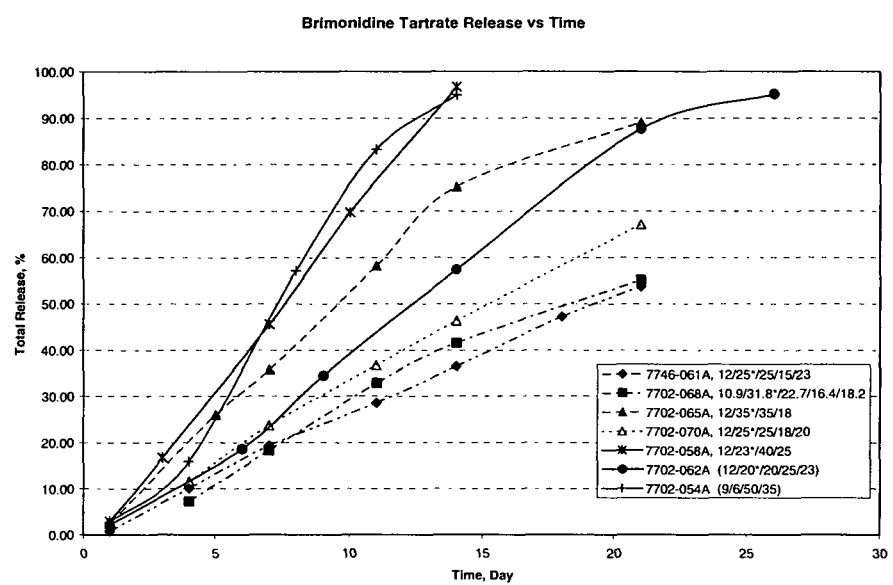

Figure 22. Release Profiles for the Table 6 Implants
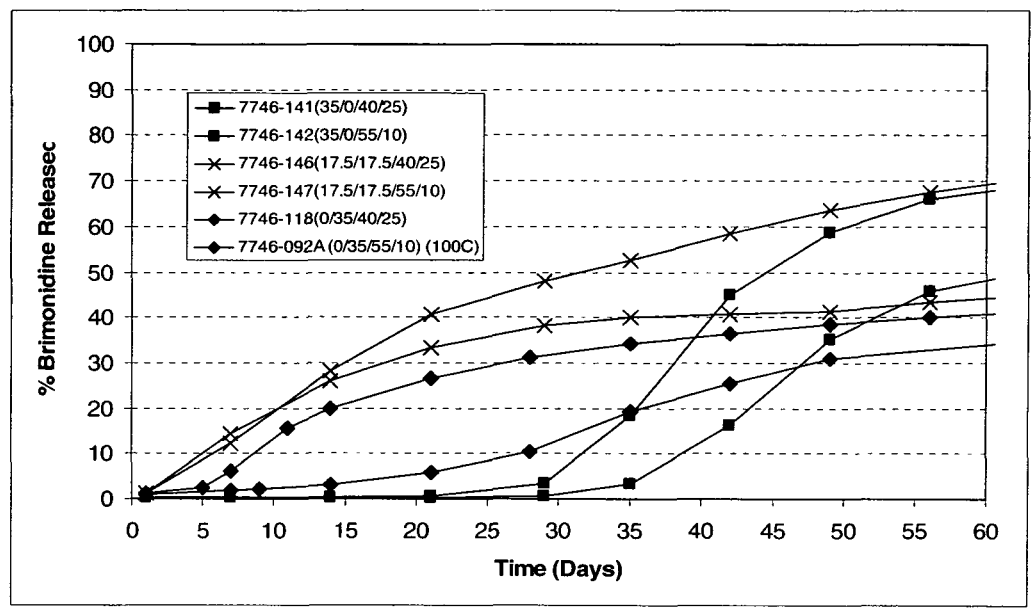

ALPHA-2 AGONIST POLYMERIC DRUG DELIVERY SYSTEMS

CROSS REFERENCE

This application is a continuation in part of application Ser. No. 11/119,021, filed Apr. 29, 2005, which is continuation in part of application Ser. No. 10/836,911 filed Apr. 30, 2004. The entire contents of these applications are incorporated herein by reference.

BACKGROUND

The present invention generally relates to devices and methods to treat an eye of a patient, and more specifically to intraocular implants that provide extended release of a therapeutic agent to an eye in which the implant is placed, and to methods of making and using such implants, for example, to treat ocular vasculopathies, or to generally improve vision.

Brimonidine, 5-bromo-6-(2-imidazolidinylideneamino) quinoxaline, is an alpha-2-selective adrenergic receptor agonist that is effective in the treatment of open-angle glaucoma by decreasing aqueous humor production and increasing uveoscleral outflow. Brimonidine is available in two chemical forms, brimonidine tartrate and brimonidine free base. Brimonidine tartrate (Alphagan P®) is commercially available from Allergan for treating glaucoma. Topical ocular brimonidine formulation, 0.15% Alphagan P® (Allergan, Irvine, Calif.), is currently commercially available for treatment of open-angle glaucoma. The solubility of brimonidine tartrate in water is 34 mg/mL, while the solubility of brimonidine freebase is negligible in water.

Recent studies have suggested that brimonidine can promote survival of injured retinal ganglion nerve cells by activation of the alpha-2-adrenoceptor in the retina and/or optic nerve. For example, brimonidine can protect injured neurons from further damage in several models of ischemia and glaucoma. See e.g. U.S. Pat. Nos. 5,856,329; 6,194,415; 6,248,741, and; 6,465,464.

Glaucoma-induced ganglion cell degeneration is one of the leading causes of blindness. This indicates that brimonidine can be utilized in a new therapeutic approach to glaucoma management in which neuroprotection and intraocular pressure reduction are valued outcomes of the therapeutic regimen. For brimonidine to protect the optic nerve, however, it must have access to the posterior segment of the eye at therapeutic levels. Currently available techniques for administering brimonidine to the posterior chamber of the eye are not sufficient to address this issue. It has been reported that intravitreal injection of brimonidine may have a neuroprotective effect. Gao H., et al., *Up-regulation of brain-derived neurotrophic factor expression by brimonidine in rat retinal ganglion cells*, Arch Ophthal 2002 June; 120(6): 797-803.

Biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493.

It would be advantageous to provide eye implantable drug delivery systems, such as intraocular implants, and methods of using such systems, that are capable of releasing a therapeutic agent at a sustained or controlled rate for extended periods of time and in amounts with few or no negative side effects.

SUMMARY

The present invention provides new drug delivery systems, and methods of making and using such systems, for extended or sustained drug release into an eye, for example, to achieve one or more desired therapeutic effects. The drug delivery systems are in the form of implants or implant elements that may be placed in an eye. The present systems and methods advantageously provide for extended release times of one or more therapeutic agents. Thus, the patient in whose eye the implant has been placed receives a therapeutic amount of an agent for a long or extended time period without requiring additional administrations of the agent. For example, the patient has a substantially consistent level of therapeutically active agent available for consistent treatment of the eye over a relatively long period of time, for example, on the order of at least about one week, such as between about two and about six months after receiving an implant. Such extended release times facilitate obtaining successful treatment results.

Intraocular implants in accordance with the disclosure herein comprise a therapeutic component and a drug release sustaining component associated with the therapeutic component. In accordance with the present invention, the therapeutic component comprises, consists essentially of, or consists of, an alpha-2 adrenergic receptor agonist. The alpha-2 adrenergic receptor agonist may be an agonist or agent that selectively activates alpha-2 adrenergic receptors, for example by binding to an alpha-2 adrenergic receptor, relative to other types of adrenergic receptors, such as alpha-1 adrenergic receptors. The selective activation can be achieved under different conditions, but preferably, the selective activation is determined under physiological conditions, such as conditions associated with an eye of a human or animal patient. The drug release sustaining component is associated with the therapeutic component to sustain release of an amount of the alpha-2 adrenergic receptor agonist into an eye in which the implant is placed. The amount of the alpha-2 adrenergic receptor agonist is released into the eye for a period of time greater than about one week after the implant is placed in the eye and is effective in preventing or reducing ocular vasculopathies, such as vascular occlusions.

In one embodiment, the intraocular implants comprise an alpha-2 adrenergic receptor agonist and a biodegradable polymer matrix. The alpha-2 adrenergic receptor agonist is associated with a biodegradable polymer matrix that degrades at a rate effective to sustain release of an amount of the agonist from the implant for a time sufficient to reduce or prevent an ocular vascular occlusion. The intraocular implant is biodegradable or bioerodible and provides a sustained release of the alpha-2 adrenergic receptor agonist in an eye for extended periods of time, such as for more than one week, for example for about three months or more and up to about six months or more. In certain implants, the alpha-2 adrenergic receptor agonist is released for about 30-35 days or less. In other implants, the alpha-2 adrenergic receptor agonist is released for 40 days or more.

The biodegradable polymer component of the foregoing implants may be a mixture of biodegradable polymers, wherein at least one of the biodegradable polymers is a polylactic acid polymer having a molecular weight less than 64 kiloDaltons (kD). Additionally or alternatively, the foregoing implants may comprise a first biodegradable polymer of a polylactic acid, and a different second biodegradable polymer of a polylactic acid. Furthermore, the foregoing implants may comprise a mixture of different biodegradable polymers, each biodegradable polymer having an inherent viscosity in a range of about 0.3 deciliters/gram (dl/g) to about 1.0 dl/g.

The alpha-2 adrenergic receptor agonist of the implants disclosed herein may include quinoxaline derivatives, or other agonists that are effective in treating ocular conditions. One example of a suitable quinoxaline derivative is brimonidine or brimonidine tartrate. In addition, the therapeutic component of the present implants may include one or more additional and different therapeutic agents that may be effective in treating an ocular condition.

A method of making the present implants involves combining or mixing the alpha-2 adrenergic receptor agonist with a biodegradable polymer or polymers. The mixture may then be extruded or compressed to form a single composition. The single composition may then be processed to form individual implants suitable for placement in an eye of a patient.

The implants may be placed in an ocular region to treat a variety of ocular conditions, including conditions such as ocular vasculopathies that affect an anterior region or posterior region of an eye. For example, the implants may be used to treat many conditions of the eye, including, without limitation, conditions associated with vascular occlusion.

Kits in accordance with the present invention may comprise one or more of the present implants, and instructions for using the implants. For example, the instructions may explain how to administer the implants to a patient, and types of conditions that may be treated with the implants.

The present invention also encompasses a biodegradable intraocular implant for improving vision. The implant can comprise an alpha-2 adrenergic receptor agonist and a biodegradable polymer. The implant releases the alpha-2 adrenergic receptor agonist from the polymer, upon intravitreal placement of the implant, in an amount effective to improve the vision of the eye in which the implant is placed. The alpha-2 adrenergic receptor agonist can be a quinoxaline, such as a (2-imidazolin-2-ylamino) quinoxaline, a 5-bromo-6(2-imidazolin-2-ylamino) quinoxaline, and derivatives thereof and mixtures thereof. Thus, the alpha-2 adrenergic receptor agonist can be a brimonidine or salts thereof or mixtures thereof. For example, the alpha-2 adrenergic receptor agonist can be brimonidine tartrate.

The alpha-2 adrenergic receptor agonist can be dispersed within the biodegradable polymer of the implant. The biodegradable polymer can comprise a mixture of a first biodegradable polymer of polylactic acid, and a different second biodegradable polymer of polylactic acid. The polymer can release drug at a rate effective to sustain release of an amount of the alpha-2 adrenergic receptor agonist from the implant for more than one month or for more that forty days or for less than thirty five days from the time the implant is placed in the vitreous of the eye.

An embodiment of the present invention is a method of making a biodegradable intraocular implant by extruding a mixture of an alpha-2 adrenergic receptor agonist and a biodegradable polymer component to form a biodegradable material that releases drug at a rate effective to sustain release of an amount of the alpha-2 adrenergic receptor agonist from the implant for a time effective to improve vision in an eye in which the implant is placed.

A further embodiment of the present invention is a method for improving or for maintaining vision by placing in the vitreous of an eye a biodegradable intraocular implant comprising an alpha-2 adrenergic receptor agonist associated with a biodegradable polymer, thereby improving or maintaining vision. This method can be used to treat an ocular condition such as: macular degeneration, macular edema, retinal arterial occlusive disease, central retinal vein occlusion, disseminated intravascular coagulopathy, branch retinal vein occlusion, hypertensive fundus changes, ocular ischemic syndrome, retinal arterial microaneurysms, hemi-retinal vein occlusion, central retinal artery occlusion, branch retinal artery occlusion, carotid artery disease (cad), eales disease, vasculopathies associated with diabetes, Non-Exudative Age Related Macular Degeneration, Exudative Age Related Macular Degeneration, Choroidal Neovascularization, Diabetic Retinopathy, Acute Macular Neuroretinopathy, Central Serous Chorioretinopathy, Cystoid Macular Edema, Diabetic Macular Edema, Acute Multifocal Placoid Pigment Epitheliopathy, Behcet's Disease, Birdshot Retinochoroidopathy, Syphilis, Lyme, Tuberculosis, Toxoplasmosis, Intermediate Uveitis, Multifocal Choroiditis, Multiple Evanescent White Dot Syndrome, Ocular Sarcoidosis, Posterior Scleritis, Serpiginous Choroiditis, Subretinal Fibrosis and Uveitis Syndrome, Vogt-Koyanagi-Harada Syndrome, Coat's Disease, Parafoveal Telangiectasia, Papillophlebitis, Frosted Branch Angiitis, Sickle Cell Retinopathy and other Hemoglobinopathies, Angioid Streaks, Familial Exudative Vitreoretinopathy, Sympathetic Ophthalmia, Uveitic Retinal Disease, Retinal Detachment, Trauma, Laser, photodynamic therapy, Photocoagulation, Hypoperfusion During Surgery, Radiation Retinopathy, Bone Marrow Transplant Retinopathy, Proliferative Vitreal Retinopathy and Epiretinal Membranes, Proliferative Diabetic Retinopathy, Ocular Histoplasmosis, Ocular Toxocariasis, Presumed Ocular Histoplasmosis Syndrome, Endophthalmitis, Toxoplasmosis, Retinal Diseases Associated with HIV Infection, Choroidal Disease Associated with HIV Infection, Uveitic Disease Associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis, Retinitis Pigmentosa, Systemic Disorders with Associated Retinal Dystrophies, Congenital Stationary Night Blindness, Cone Dystrophies, Stargardt's Disease and Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum, Retinal Detachment, Macular Hole, Giant Retinal Tear, Retinal Disease Associated with Tumors, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors, Punctate Inner Choroidopathy, Acute Posterior Multifocal Placoid Pigment Epitheliopathy, Myopic Retinal Degeneration, and Acute Retinal Pigment Epithelitis.

Notably, the method can improve vision in a normal eye. A normal eye is an eye which is not diseased or damaged. For example, the method can improve vision (as by improving visual acuity) in a normal eye by up to about 56%. The method can also improve vision in an eye with an ocular condition. For example, the method can improve vision in an eye with an ocular condition by up to about 23%. The ocular condition can be a vasculopathy. Alternately, the ocular condition can be due to an elevated intraocular pressure and/or the ocular condition can be a retinal ischemic injury.

The implant can release the alpha-2 adrenergic receptor agonist from the polymer, upon intravitreal placement of the implant, for a period of about ninety days. Significantly, the alpha-2 adrenergic receptor agonist can be retained in the retina for a period of time longer than it is retained in the vitreous. An embodiment of the present invention is a method for improving, maintaining, restoring or repairing vision, the method comprising the step of placing in the vitreous of an eye a biodegradable intraocular implant comprising a brimonidine associated with a biodegradable polymer, thereby improving, maintaining, restoring or repairing vision.

An embodiment of our invention is a biodegradable intraocular implant comprising an alpha-2 adrenergic receptor agonist and a biodegradable polymer, wherein the biodegradable polymer comprises an ester end-capped biodegradable polymer and an acid end-capped biodegradable polymer. The implant can comprise from about 10% to about 91% ester end-capped biodegradable polymer, from about 5 wt % to about 40 wt % acid end-capped biodegradable polymer, and from about 4 wt % to about 50 wt % alpha-2 adrenergic receptor agonist. Preferably, the implant can comprise from about 45% to about 80% ester end-capped biodegradable polymer, from about 10 wt % to about 40 wt % acid end-capped biodegradable polymer, and about 10 wt % to about 15 wt % alpha-2 adrenergic receptor agonist. More preferably, the implant can comprise about 88 wt % ester end-capped biodegradable polymer, about 10 wt % acid end-capped biodegradable polymer, and about 12 wt % alpha-2 adrenergic receptor agonist. Most preferably, the implant can comprise from about 53 wt % to about 73% ester end-capped biodegradable polymer, from about 15 wt % to about 35 wt % acid end-capped biodegradable polymer, and from about 9 wt % to about 12 wt % alpha-2 adrenergic receptor agonist.

The biodegradable polymer of the implant can comprise more than one ester end-capped biodegradable polymer. Alternately, the biodegradable polymer of the implant can comprise more than one acid end-capped biodegradable polymer. The implant can have no or a nominal lag time after ocular implantation or insertion of the implant before release of a therapeutically effective amount of the alpha-2 adrenergic receptor agonist from the implant occurs. The implant comprise greater than or equal to 4 weight percent (wt %) of a biologically active alpha-2 adrenergic receptor agonist and the implant preferably does not include any pore forming additives, release rate modulators or release rate modifiers. The implant can exhibit a sustained release of the alpha-2 adrenergic receptor agonist from the biodegradable polymeric matrix over a period of at least 115 days. Additionally, the implant can exhibit a substantially linear release of the alpha-2 adrenergic receptor agonist from the biodegradable polymeric matrix of the implant over a period of time of from about 20 days to about 50 days.

A preferred embodiment of a biodegradable intraocular implant within the scope of our invention can comprise an alpha-2 adrenergic receptor agonist, and a biodegradable polymer, wherein the biodegradable polymer comprises an ester end-capped biodegradable polymer and an acid end-capped biodegradable polymer, wherein the implant comprises from about 40% to about 91% of at least two different ester end-capped biodegradable polymers, from about 5 wt % to about 40 wt % acid end-capped biodegradable polymer, and from about 4 wt % to about 20 wt % alpha-2 adrenergic receptor agonist.

Our invention also includes a process for making a biodegradable intraocular implant by mixing an alpha-2 adrenergic receptor agonist and a biodegradable polymer, wherein the biodegradable polymer comprises an ester end-capped biodegradable polymer and an acid end-capped biodegradable polymer; heating the mixture, and; extruding the heated mixture, to thereby make a biodegradable intraocular implant.

An implant within the scope of our invention can be an extruded filament with a diameter of about 0.5 mm, a length of about 6 mm and a weight of about 1 mg. The alpha-2 adrenergic receptor agonist can be homogenously distributed throughout the implant.

Our implants can be used to treat ocular conditions by intraocular administration of a biodegradable intraocular implant comprising an alpha-2 adrenergic receptor agonist and a biodegradable polymer, wherein the biodegradable polymer comprises an ester end-capped biodegradable polymer and an acid end-capped biodegradable polymer. The alpha-2 adrenergic receptor agonist can be selected from the group consisting of brimonidine, salts thereof, and mixtures thereof.

In another embodiment of our invention a biodegradable intraocular implant can comprise a plurality of forms of an alpha-2 adrenergic receptor agonist and a biodegradable polymer. The alpha-2 adrenergic receptor agonist can be a brimonidine and the brimonidine can be present in two forms in the implant. The two forms of brimonidine present in the implant can be brimonidine free base and brimonidine tartrate. Such and implant can comprises from about 50 wt % to about 70% ester end-capped biodegradable polymer, from about 1 wt % to about 49 wt % brimonidine free base and from about 1 wt % to about 49 wt % brimonidine tartrate. Alternately, the implant can comprises from about 50 wt % to about 60% ester end-capped biodegradable polymer, from about 1 wt % to about 49 wt % brimonidine free base and from about 1 wt % to about 49 wt % brimonidine tartrate. More preferably, the implant can comprise from about 50 wt % to about 70% ester end-capped biodegradable polymer, from about 10 wt % to about 30 wt % brimonidine free base and from about 10 wt % to about 30 wt % brimonidine tartrate. In most preferred embodiment the implant can comprise from about 55 wt % to about 65% ester end-capped biodegradable polymer, from about 15 wt % to about 20 wt % brimonidine free base and from about 15 wt % to about 20 wt % brimonidine tartrate, for example the implant can comprise about 65 wt % ester end-capped biodegradable polymer, about 18 wt % brimonidine free base and about 18 wt % brimonidine tartrate. The implant of claim 21, wherein the biodegradable polymer comprises more than one ester end-capped biodegradable polymer. And the implant can have no burst effect and no or a nominal lag time after ocular implantation or insertion of the implant before release of a therapeutically effective amount of the alpha-2 adrenergic receptor agonist from the implant occurs. Additionally, the implant can exhibit a sustained release of the alpha-2 adrenergic receptor agonist from the biodegradable polymeric matrix over a period of at least 60 days. Furthermore, the implant can exhibits a substantially linear release of the alpha-2 adrenergic receptor agonist from the biodegradable polymeric matrix of the implant over a period of time of from about 20 days to about 50 days.

A preferred embodiment of our invention can comprise a brimonidine free base; a brimonidine tartrate, and an ester end-capped biodegradable polymer, wherein the implant comprises from about 50 wt % to about 70% of the ester end-capped biodegradable polymer, from about 1 wt % to about 49 wt % of the brimonidine free base and from about 1 wt % to about 49 wt % of the brimonidine tartrate.

Our invention encompasses a process for making a biodegradable intraocular implant comprising (a) mixing a plurality of forms of alpha-2 adrenergic receptor agonist and a biodegradable polymer; (b) heating the mixture, and; (c) extruding the heated mixture, to thereby make a biodegradable intraocular implant. The implant can be extruded as a filament with a diameter of about 0.5 mm, a length of about 6 mm and a weight of about 1 mg. The implant can also be made by a direct compression or solvent extraction method. The shape of the implant can also be as a tablet, pellet or rod.

Finally, our invention encompasses a method of treating a symptom of glaucoma by placing a biodegradable intraocular implant comprising an alpha-2 adrenergic receptor agonist associated with a biodegradable polymer into the vitreous of an eye, thereby treating a symptom of the glaucoma. The symptom of the glaucoma can be reduced for at least about 35 days after intravitreal placement of the implant. The symptom of the glaucoma treated can be an elevated intraocular pressure.

Additional aspects and advantages of the present invention are set forth in the following description and claims, particularly when considered in conjunction with the accompanying drawings.

DRAWINGS

The patent or application file contains at least one drawing executed in color. Copies of this patent or patent application publication with color drawing(s) will be provided by the Office upon request and payment of the necessary fee.

FIG. 18 is a graph which illustrates three different possible release profiles for the release of an active agent from an implant. Amount of an active agent released is shown on the Y-axis while the X-axis represents time after intraocular placement of the implant.

FIG. 19 is a graph showing the percent of the total amount of brimonidine released (Y-axis) versus time (X-axis) in days for a period of 21 days in vitro for the three Table 4 implants.

FIG. 20 is a graph showing the percent of the total amount of brimonidine released (Y-axis) versus time in days (X-axis) for a period of 151 days in vitro for the Table 4 implant 7746-073.

FIG. 21 is a graph showing the percent of the total amount of brimonidine released (Y-axis) versus time (X-axis) in days for a period of 14-26 days in vitro for the seven the Table 5 implants.

FIG. 22 is a graph showing the percent of the total amount of brimonidine released (Y-axis) versus time (X-axis) in days over a period of 60 days in vitro for the six Table 6 implants.

DESCRIPTION

Figure 1:
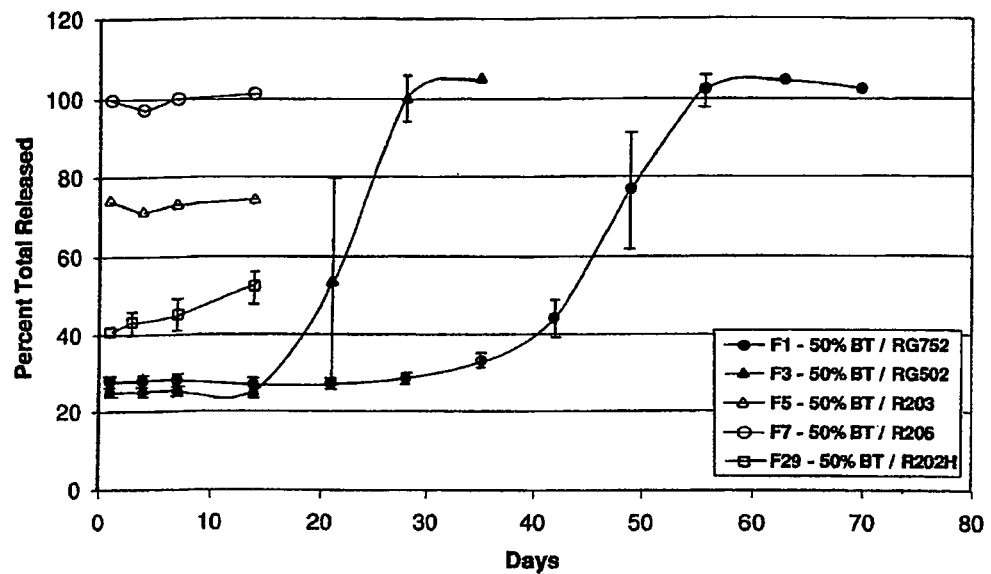
FIG. 1 is a graph showing the cumulative release profiles for biodegradable brimonidine tartrate containing implants as determined in 0.9% phosphate buffered saline at 37 degrees Celsius.

As described herein, controlled and sustained administration of a therapeutic agent through the use of one or more intraocular implants may improve treatment of undesirable ocular conditions. The implants comprise a pharmaceutically acceptable polymeric composition and are formulated to release one or more pharmaceutically active agents, such as alpha-2 adrenergic receptor agonists, over an extended period of time. The implants are effective to provide a therapeutically effective dosage of the agent or agents directly to a region of the eye to treat or prevent one or more undesirable ocular conditions. Thus, with a single administration, therapeutic agents will be made available at the site where they are needed and will be maintained for an extended period of time, rather than subjecting the patient to repeated injections or, in the case of self-administered drops, ineffective treatment with only limited bursts of exposure to the active agent or agents.

An intraocular implant in accordance with the disclosure herein comprises a therapeutic component and a drug release sustaining component associated with the therapeutic component. In accordance with the present invention, the therapeutic component comprises, consists essentially of, or consists of, an alpha-2 adrenergic receptor agonist. The drug release sustaining component is associated with the therapeutic component to sustain release of a therapeutically effective amount of the alpha-2 adrenergic receptor agonist into an eye in which the implant is placed. The therapeutic amount of the alpha-2 adrenergic receptor agonist is released into the eye for a period of time greater than about one week after the implant is placed in the eye.

Definitions

For the purposes of this description, we use the following terms as defined in this section, unless the context of the word indicates a different meaning.

"About" means plus or minus ten percent of the value so qualified.

"Biocompatible" means that there is an insignificant inflammatory response upon contact of the biocompatible material with an ocular tissue.

"Effective amount" as applied to an active agent means that amount of the compound which is generally sufficient to effect a desired change in the subject.

"Intraocular implant" means a device or element that is structured, sized, or otherwise configured to be placed in an eye. Intraocular implants are generally biocompatible with physiological conditions of an eye and do not cause adverse side effects. Intraocular implants may be placed in an eye without disrupting vision of the eye.

"Therapeutic component" means a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in an eye.

"Drug release sustaining component" means a portion of the intraocular implant that is effective to provide a sustained release of the therapeutic agents of the implant. A drug release sustaining component may be a biodegradable polymer matrix, or it may be a coating covering a core region of the implant that comprises a therapeutic component.

"Associated with" means mixed with, dispersed within, coupled to, covering, or surrounding.

"Ocular region" or "ocular site" means any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

"Ocular condition" means a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

"Biodegradable polymer" means a polymer or polymers which degrade in vivo, and wherein erosion of the polymer or polymers over time is occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

"Treat", "treating", or "treatment" means a reduction or resolution or prevention of an ocular condition, ocular injury or damage, or to promote healing of injured or damaged ocular tissue.

"Therapeutically effective amount" means the level or amount of agent needed to treat an ocular condition, or reduce or prevent ocular injury or damage without causing significant negative or adverse side effects to the eye or a region of the eye.

Intraocular implants have been developed which can release drug loads over various' time periods. These implants, which when inserted into an eye, such as the vitreous of an eye, provide therapeutic levels of an alpha-2 adrenergic receptor agonist for extended periods of time (e.g., for about 1 week or more). The implants disclosed are effective in treating ocular conditions, such as posterior ocular conditions.

In one embodiment of the present invention, an intraocular implant comprises a biodegradable polymer matrix. The biodegradable polymer matrix is one type of a drug release sustaining component. The biodegradable polymer matrix is effective in forming a biodegradable intraocular implant. The biodegradable intraocular implant comprises an alpha-2 adrenergic receptor agonist associated with the biodegradable polymer matrix. The matrix degrades at a rate effective to sustain release of an amount of the alpha-2 adrenergic receptor agonist for a time greater than about one week from the time in which the implant is placed in ocular region or ocular site, such as the vitreous of an eye.

The alpha-2 adrenergic receptor agonist of the implant is typically an agent that selectively activates alpha-2 adrenergic receptors relative to alpha-1 adrenergic receptors. In certain implants, the alpha-2 adrenergic receptor agonist is selectively activates a subtype of the alpha-2 adrenergic receptors. For example, the agonist may selectively activate one or more of the alpha-2a, the alpha-2b, or the alpha-2c receptors, under certain conditions, such as physiological conditions. Under other conditions, the agonist of the implant may not be selective for alpha-2 adrenergic receptor subtypes. The agonist may activate the receptors by binding to the receptors, or by any other mechanism.

In certain implants, the alpha-2 adrenergic receptor agonist is a quinoxaline derivative. The quinoxaline derivatives useful in the present implants are those quinoxaline derivatives having the formula,

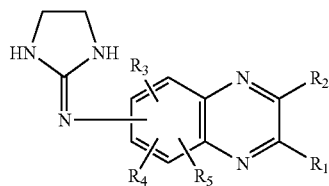

pharmaceutically acceptable acid addition salts thereof, and mixtures thereof. $R_1$ and $R_2$ each is independently selected from the group consisting of H, alkyl radicals containing 1 to 4 carbon atoms and alkoxy radicals containing 1 to 4 carbon atoms. $R_2$ is preferably a methyl radical. The 2-imidazolin-2-ylamino group may be in any of the 5-, 6-, 7- and 8-positions, preferably in the 6-position, of the quinoxaline nucleus. $R_3$, $R_4$ and $R_5$ each is located in one of the remaining 5-, 6-, 7- or 8-positions of the quinoxaline nucleus and is independently selected from the group consisting of Cl, Br, H and alkyl radicals containing 1 to 3 carbon atoms. $R_3$ is preferably in the 5-position of the quinoxaline nucleus, and $R_4$ and $R_5$ are preferably both H. In a particularly useful embodiment $R_3$ is Br.

In at least one implant, $R_1$ is H and $R_2$ is selected from alkyl radicals containing 1 to 4 carbon atoms. $R_3$ may advantageously be in the 5-position of the quinoxaline nucleus and be selected from H and alkyl radicals containing 1 to 3 carbon atoms. All stereoisomers, tautomers and mixtures thereof which comply with the constraints of one or more of the presently useful compounds are included within the scope of the present invention.

Pharmaceutically acceptable acid addition salts of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

In more specific implants, the quinoxaline derivative has the formula

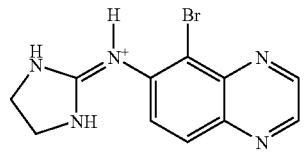 [SMILES: Brc1c([NH+]=C2NCCN2)ccc2nccnc12]

In additional implants, the alpha-2 adrenergic receptor agonist is provided as a salt having the formula

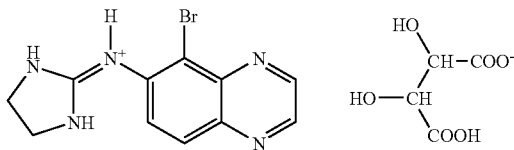

The foregoing salt is known as brimonidine tartrate (AGN 190342-F, 5-bromo-6-(2-imidazolidinylidene amino) quinoxaline tartrate), and is publicly available from Allergan, Inc. under the tradename Alphagan-P®. Brimonidine, an organic base, is publicly available as either brimonidine tartrate salt or as brimonidine freebase. The tartrate salt is more soluble than the freebase in various aqueous media. Since both the tartrate salt and the freebase are chemically stable and have melting points higher than 200° C., both forms are suitable in forming the present implants.

Thus, the implant may comprise a therapeutic component which comprises, consists essentially of, or consists of a brimonidine salt, such as brimonidine tartrate, a brimonidine free base, or mixtures thereof.

The alpha-2 adrenergic receptor agonist may be in a particulate or powder form and entrapped by the biodegradable polymer matrix. Usually, alpha-2 adrenergic receptor agonist particles will have an effective average size less than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers.

The alpha-2 adrenergic receptor agonist of the implant is preferably from about 10% to 90% by weight of the implant. More preferably, the alpha-2 adrenergic receptor agonist is from about 20% to about 80% by weight of the implant. In a preferred embodiment, the alpha-2 adrenergic receptor agonist comprises about 20% by weight of the implant (e.g., 15%-25%). In another embodiment, the alpha-2 adrenergic receptor agonist comprises about 50% by weight of the implant.

Suitable polymeric materials or compositions for use in the implant include those materials which are compatible, that is biocompatible, with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 64 kD, usually from about 10 to about 54 kD, and more usually from about 12 to about 45 kD.

In some implants, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The % of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the intraocular implant may comprise a mixture of two or more biodegradable polymers. For example, the implant may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or combination of both. As discussed herein, the matrix of the intraocular implant may release drug at a rate effective to sustain release of an amount of the alpha-2 adrenergic receptor agonist for more than one week after implantation into an eye. In certain implants, therapeutic amounts of the alpha-2 adrenergic receptor agonist are released for no more than about 30-35 days after implantation. For example, an implant may comprise brimonidine tartrate, and the matrix of the implant degrades at a rate effective to sustain release of a therapeutically effective amount of brimonidine tartrate for about one month after being placed in an eye. As another example, the implant may comprise brimonidine tartrate, and the matrix releases drug at a rate effective to sustain release of a therapeutically effective amount of brimonidine tartrate for more than forty days, such as for about six months.

One example of the biodegradable intraocular implant comprises an alpha-2 adrenergic receptor agonist associated with a biodegradable polymer matrix, which comprises a mixture of different biodegradable polymers. At least one of the biodegradable polymers is a polylactide having a molecular weight of about 63.3 kD. A second biodegradable polymer is a polylactide having a molecular weight of about 14 kD. Such a mixture is effective in sustaining release of a therapeutically effective amount of the alpha-2 adrenergic receptor agonist for a time period greater than about one month from the time the implant is placed in an eye.

Another example of a biodegradable intraocular implant comprises an alpha-2 adrenergic receptor agonist associated with a biodegradable polymer matrix, which comprises a mixture of different biodegradable polymers, each biodegradable polymer having an inherent viscosity from about 0.16 dl/g to about 1.0 dl/g. For example, one of the biodegradable polymers may have an inherent viscosity of about 0.3 dl/g. A second biodegradable polymer may have an inherent viscosity of about 1.0 dl/g. The inherent viscosities identified above may be determined in 0.1% chloroform at 25° C.

One particular implant comprises brimonidine tartrate associated with a combination of two different polylactide polymers. The brimonidine tartrate is present in about 20% by weight of the implant. One polylactide polymer has a molecular weight of about 14 kD and an inherent viscosity of about 0.3 dl/g, and the other polylactide polymer has a molecular weight of about 63.3 kD and an inherent viscosity of about 1.0 dl/g. The two polylactide polymers are present in the implant in a 1:1 ratio. Such an implant provides for release of the brimonidine for more than two months in vitro, as described herein. The implant is provided in the form of a rod or a filament produced by an extrusion process.

The release of the alpha-2 adrenergic receptor agonist from the intraocular implant comprising a biodegradable polymer matrix may include an initial burst of release followed by a gradual increase in the amount of the alpha-2 adrenergic receptor agonist released, or the release may include an initial delay in release of the alpha-2 adrenergic receptor agonist followed by an increase in release. When the implant is substantially completely degraded, the percent of the alpha-2 adrenergic receptor agonist that has been released is about one hundred. Compared to existing implants, the implants disclosed herein do not completely release, or release about 100% of the alpha-2 adrenergic receptor agonist, until after about one week of being placed in an eye.

It may be desirable to provide a relatively constant rate of release of the alpha-2 adrenergic receptor agonist from the implant over the life of the implant. For example, it may be desirable for the alpha-2 adrenergic receptor agonist to be released in amounts from about 0.01 μg to about 2 μg per day for the life of the implant. However, the release rate may change to either increase or decrease depending on the formulation of the biodegradable polymer matrix. In addition, the release profile of the alpha-2 adrenergic receptor agonist may include one or more linear portions and/or one or more non-linear portions. Preferably, the release rate is greater than zero once the implant has begun to degrade or erode.

The implants may be monolithic, i.e. having the active agent or agents homogenously distributed through the polymeric matrix, or encapsulated, where a reservoir of active agent is encapsulated by the polymeric matrix or as a core-shell type of implant. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including the alpha-2 adrenergic receptor agonist, may be distributed in a non-homogenous pattern in the matrix. For example, the implant may include a portion that has a greater concentration of the alpha-2 adrenergic receptor agonist relative to a second portion of the implant.

The intraocular implants disclosed herein may have a size of between about 5 μm and about 2 mm, or between about 10 μm and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 μg, more preferably about 500-1000 μg. For example, an implant may be about 500 μg, or about 1000 μg. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Thus, implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of 0.5 μm to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

The proportions of alpha-2 adrenergic receptor agonist, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the alpha-2 adrenergic receptor agonist or alpha-2 adrenergic receptor agonists included in the intraocular implants disclosed herein, the intraocular implants may also include one or more additional ophthalmically acceptable therapeutic agents. For example, the implant may include one or more antihistamines, one or more antibiotics, one or more beta blockers, one or more steroids, one or more antineoplastic agents, one or more immunosuppressive agents, one or more antiviral agents, one or more antioxidant agents, and mixtures thereof.

Pharmacologic or therapeutic agents which may find use in the present systems, include, without limitation, those disclosed in U.S. Pat. Nos. 4,474,451, columns 4-6 and 4,327,725, columns 7-8.

Examples of antihistamines include, and are not limited to, loratadine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimeprazine doxylamine, pheniramine, pyrilamine, chlorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

Examples of beta blockers include acebutolol, atenolol, labetalol, metoprolol, propranolol, timolol, and derivatives thereof.

Examples of steroids include corticosteroids, such as cortisone, prednisolone, fluorometholone, dexamethasone, medrysone, loteprednol, fluazacort, hydrocortisone, prednisone, betamethasone, prednisone, methylprednisolone, triamcinolone hexacetonide, paramethasone acetate, diflorasone, fluocinonide, fluocinolone, triamcinolone, derivatives thereof, and mixtures thereof.

Examples of antineoplastic agents include adriamycin, cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valaciclovir, dideoxycytidine, phosphonoformic acid, ganciclovir, and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryptoxanthin, astaxanthin, lycopene, N-acetyl-cysteine, carnosine, gamma-glutamyl-cysteine, quercetin, lactoferrin, dihydrolipoic acid, citrate, Ginkgo Biloba extract, tea catechins, bilberry extract, vitamins E or esters of vitamin E, retinyl palmitate, and derivatives thereof.

Other therapeutic agents include squalamine, carbonic anhydrase inhibitors, alpha agonists, prostamides, prostaglandins, antiparasitics, antifungals, and derivatives thereof.

The amount of active agent or agents employed in the implant, individually or in combination, will vary widely depending on the effective dosage required and the desired rate of release from the implant. Usually the agent will be at least about 1, more usually at least about 10 weight percent of the implant, and usually not more than about 80, more usually not more than about 40 weight percent of the implant.

In addition to the therapeutic component, the intraocular implants disclosed herein may include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight. In at least one of the present implants, a purite preservative is provided in the implant, such as when the alpha-2 adrenergic receptor agonist is brimonidine. Thus, these implants may contain a therapeutically effective amount of Alphagan-P®.

In some situations mixtures of implants may be utilized employing the same or different pharmacological agents. In this way, a cocktail of release profiles, giving a biphasic or triphasic release with a single administration is achieved, where the pattern of release may be greatly varied.

Additionally, release modulators such as those described in U.S. Pat. No. 5,869,079 may be included in the implants. The amount of release modulator employed will be dependent on the desired release profile, the activity of the modulator, and on the release profile of the alpha-2 adrenergic receptor agonist in the absence of modulator. Electrolytes such as sodium chloride and potassium chloride may also be included in the implant. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

In certain implants, an implant comprising brimonidine or brimonidine tartrate and a biodegradable polymer matrix is able to release or deliver an amount of brimonidine between about 0.1 mg to about 0.5 mg for about 3-6 months after implantation into the eye. The implant may be configured as a rod or a wafer. A rod-shaped implant may be derived from filaments extruded from a 720 μm nozzle and cut into 1 mg size. A wafer-shaped implant may be a circular disc having a diameter of about 2.5 mm, a thickness of about 0.127 mm, and a weight of about 1 mg.

The proposed 3-month release formulations may be sterile, and bioerodible in the form of a rod, a wafer or a microsphere containing brimonidine tartrate within a PLA matrix or POE matrix. The implants are designed to delay the clearance of the drug and reduce the need for repeated implantation over 3-month period, thereby lowering the risk of complications.

Various techniques may be employed to produce the implants described herein. Useful techniques include, but are not necessarily limited to, solvent evaporation methods, phase separation methods, interfacial methods, molding methods, injection molding methods, extrusion methods, co-extrusion methods, carver press method, die cutting methods, heat compression, combinations thereof and the like.

Specific methods are discussed in U.S. Pat. No. 4,997,652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes. For example, a time period may be about 10 minutes, preferably about 0 to 5 min. The implants are then extruded at a temperature of about 60 degrees C. to about 130 degrees C., such as about 75 degrees C.

In addition, the implant may be coextruded so that a coating is formed over a core region during the manufacture of the implant.

Compression methods may be used to make the implants, and typically yield implants with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

The implants of the present invention may be inserted into the eye, for example the vitreous chamber of the eye, by a variety of methods, including placement by forceps or by trocar following making a 2-3 mm incision in the sclera. One example of a device that may be used to insert the implants into an eye is disclosed in U.S. Patent Publication No. 2004/0054374. The method of placement may influence the therapeutic component or drug release kinetics. For example, delivering the implant with a trocar may result in placement of the implant deeper within the vitreous than placement by forceps, which may result in the implant being closer to the edge of the vitreous. The location of the implant may influence the concentration gradients of therapeutic component or drug surrounding the element, and thus influence the release rates (e.g., an element placed closer to the edge of the vitreous may result in a slower release rate).

The present implants are configured to release an amount of alpha-2 adrenergic receptor agonist in an eye for a period of time to minimize an ocular vascular occlusion, such as a retinal vascular occlusion. Retinal vascular occlusion may result from a variety of diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, hemi-retinal vein occlusion, central retinal artery occlusion, branch retinal artery occlusion, carotid artery disease (cad), eales disease and vasculopathies associated with diabetes. By implanting the alpha-2 adrenergic receptor agonist-containing implants into the vitreous of an eye, it is believed that the agonist is effective to reduce occlusion within blood vessels located in the eye.

In addition, the present implants may be configured to release an alpha-2 adrenergic receptor agonist in a therapeutically effective amount for a period of time effective to treat glaucoma of a patient.

The implants disclosed herein may also be configured to release additional therapeutic agents, as described above, which may be effective in treating diseases or conditions, such as the following:

Maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpiginous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasia, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

In one embodiment, an implant, such as the implants disclosed herein, is administered to a posterior segment of an eye of a human or animal patient, and preferably, a living human or animal. In at least one embodiment, an implant is administered without accessing the subretinal space of the eye. For example, a method of treating a patient may include placing the implant directly into the posterior chamber of the eye. In other embodiments, a method of treating a patient may comprise administering an implant to the patient by at least one of intravitreal injection, subconjunctival injection, sub-tenon injections, retrobulbar injection, and suprachoroidal injection.

In at least one embodiment, a method of reducing retinal vascular occlusion in a patient comprises administering one or more implants containing one or more alpha-2 adrenergic receptor agonists, as disclosed herein to a patient by at least one of intravitreal injection, subconjunctival injection, sub-tenon injection, retrobulbar injection, and suprachoroidal injection. A syringe apparatus including an appropriately sized needle, for example, a 27 gauge needle or a 30 gauge needle, can be effectively used to inject the composition with the posterior segment of an eye of a human or animal. Repeat injections are often not necessary due to the extended release of the alpha-2 adrenergic receptor agonists from the implants.

In another aspect of the invention, kits for treating an ocular condition of the eye are provided, comprising: a) a container comprising an extended release implant comprising a therapeutic component including an alpha-2 adrenergic receptor agonist, such as brimonidine free base or brimonidine tartrate (e.g., Alphagan-P®), and a drug release sustaining component; and b) instructions for use. Instructions may include steps of how to handle the implants, how to insert the implants into an ocular region, and what to expect from using the implants.

Example 1

Manufacture and Testing of Implants Containing Brimonidine and a Biodegradable Polymer Matrix Biodegradable implants were made by combining brimonidine tartrate or brimonidine freebase with a biodegradable polymer composition in a stainless, steel mortar. The combination was mixed via a Turbula shaker set at 96 RPM for 15 minutes. The powder blend was scraped off the wall of the mortar and then remixed for an additional 15 minutes. The mixed powder blend was heated to a semi-molten state at specified temperature for a total of 30 minutes, forming a polymer/drug melt.

Rods were manufactured by pelletizing the polymer/drug melt using a 9 gauge polytetrafluoroethylene (PTFE) tubing, loading the pellet into the barrel and extruding the material at the specified core extrusion temperature into filaments. The filaments were then cut into about 1 mg size implants or drug delivery systems. The rods had dimensions of about 2 mm long×0.72 mm diameter. The rod implants weighed between about 900 µg and 1100 µg.

Wafers were formed by flattening the polymer melt with a Carver press at a specified temperature and cutting the flattened material into wafers, each weighing about 1 mg. The wafers had a diameter of about 2.5 mm and a thickness of about 0.13 mm. The wafer implants weighed between about 900 µg and 1100 µg.

The in-vitro release testing was performed on each lot of implant (rod or wafer) in six replicates initially, and later in four replicates. Each implant was placed into a 24 mL screw cap vial with 10 mL of Phosphate Buffered Saline solution at 37° C. and 1 mL aliquots were removed and replaced with equal volume of fresh medium on day 1, 4, 7, 14, 28, and every two weeks thereafter.

The drug assays were performed by HPLC, which consists of a Waters 2690 Separation Module (or 2696), and a Waters 2996 Photodiode Array Detector. An Ultrasphere, C-18 (2), 5 µm; 4.6×150 mm column heated at 30° C. was used for separation and the detector was set at 264 nm. The mobile phase was (10:90) MeOH—buffered mobile phase with a flow rate of 1 mL/min and a total run time of 12 min per sample. The buffered mobile phase comprised of (68:0.75: 0.25:31) 13 mM 1-Heptane Sulfonic Acid, sodium salt-glacial acetic acid-triethylamine-Methanol. The release rates were determined by calculating the amount of drug being released in a given volume of medium over time in µg/day.

The polymers chosen for the implants are were obtained from Boehringer Ingelheim. The polymers were: RG502, RG752, R202H, R203 and R206, and Purac PDLG (50/50). RG502 is (50:50) poly(D,L-lactide-co-glycolide), RG752 is (75:25) poly(D,L-lactide-co-glycolide), R202H is 100% poly (D, L-lactide) with acid end group or terminal acid groups, R203 and R206 are both 100% poly(D, L-lactide). Purac PDLG (50/50) is (50:50) poly(D,L-lactide-co-glycolide). The inherent viscosity of RG502, RG752, R202H, R203, R206, and Purac PDLG are 0.2, 0.2, 0.2, 0.3, 1.0, and 0.2 dL/g, respectively. The average molecular weight of RG502, RG752, R202H, R203, R206, and Purac PDLG are, 11700, 11200, 6500, 14000, 63300, and 9700 Daltons, respectively.

A total of 53 formulations were prepared, 31 rods and 22 wafers. Of the rod formulations, 4 had release periods longer than 3 months and 3 had release periods longer than 6 months. Of the wafer formulations, 7 had release periods longer than 3 months and 4 had release periods longer than 4 months.

A list of the rod formulations is shown in Table 1, and a list of wafer formulations is shown in Table 2.

TABLE 1

Brimonidine Rod Formulations

| Formulation | Lot | BT (w/w) | BFB (w/w) | Polymer | I.V. (dL/g) | Core Extr T |
|---|---|---|---|---|---|---|
| 1 | 295-123 | 50% |  | RG752 | 0.2 | 104° C. |
| 2 | 295-124 |  | 50% | RG752 | 0.2 | 105° C. |
| 3 | 295-126 | 50% |  | RG502 | 0.2 | 108° C. |
| 4 | 295-127 |  | 50% | RG502 | 0.2 | 112° C. |
| 5 | 295-167 | 50% |  | R203 | 0.3 | 98° C. |

TABLE 1-continued

Brimonidine Rod Formulations

| Formulation | Lot | BT (w/w) | BFB (w/w) | Polymer | I.V. (dL/g) | Core Extr T |
|---|---|---|---|---|---|---|
| 6 | 295-168 | | 50% | R203 | 0.3 | 101° C. |
| 7 | 295-169 | 50% | | R206 | 1.0 | 118° C. |
| 8 | 295-170 | | 50% | R206 | 1.0 | 104° C. |
| 9 | 295-171 | 25% | | R206 | 1.0 | 98° C. |
| 10 | 295-172 | 25% | | R203 | 0.3 | 96° C. |
| 11 | 453-3 | 10% | 40% | R203 | 0.3 | 98° C. |
| 12 | 453-4 | 5% | 20% | R203 | 0.3 | 96° C. |
| 13 | 453-6 | 10% | 40% | R206 | 1.0 | 105° C. |
| 14 | 453-7 | 5% | 20% | R206 | 1.0 | 104° C. |
| 15 | 453-8 | 5% | 45% | R206 | 1.0 | 102° C. |
| 16 | 453-9 | 15% | | R206 | 1.0 | 102° C. |
| 17 | 453-10 | 20% | | (1:1) R203/R206 | N/A | 98° C. |
| 18 | 453-11 | 20% | | (3:1) R203/R206 | N/A | 96° C. |
| 19 | 453-12 | 10% | 40% | RG752 | 0.2 | 108° C. |
| 20 | 453-13 | 5% | 20% | RG752 | 0.2 | 104° C. |
| 24 | 453-50 | 20% | | R206 | 1.0 | 100° C. |
| 25 | 453-51 | 17% | | (1:1) R203/R206 | N/A | 98° C. |
| 26 | 453-52 | | 40% | (1:1) RG752/RG502 | N/A | 105° C. |
| 27 | 453-53 | | 40% | (3:1) RG752/RG502 | N/A | 103° C. |
| 28 | 453-54 | | 40% | (1:1) R203/RG502 | N/A | 103° C. |
| 29 | 453-55 | 50% | | R202H | 0.2 | 96° C. |
| 30 | 453-56 | | 50% | R202H | 0.2 | 98° C. |
| 31 | 453-73 | 20% | | RG752 | 0.2 | 98° C. |
| 32 | 453-74 | 20% | | Purac (Mw 9700) | N/A | 95° C. |
| 33 | 453-75 | | 20% | Purac (Mw 9700) | N/A | 92° C. |
| 53 | 453-95 | 20% | | (2:1) R203/R206 | N/A | 97° C. |

BT = Brimonidine Tartrate
BFB = Brimonidine Free Base
I.V. = Inherent Viscosity

TABLE 2

Brimonidine wafer Formulations

| Formulation | Lot | BT (w/w) | BFB (w/w) | Polymer | I.V. (dL/g) |
|---|---|---|---|---|---|
| 21 | 453-47 | 25% | | R206 | 1.0 |
| 22 | 453-48 | 20% | | (1:1) R203/R206 | N/A |
| 23 | 453-49 | 20% | | (3:1) R203/R206 | N/A |
| 34 | 453-76 | | 20% | (1:1) R203/R206 | N/A |
| 35 | 453-77 | | 25% | R206 | 1.0 |
| 36 | 453-78 | | 20% | (3:1) R203/R206 | N/A |
| 37 | 453-79 | | 25% | R203 | 0.3 |
| 38 | 453-80 | | 50% | R203 | 0.3 |
| 39 | 453-81 | | 50% | R206 | 1.0 |
| 40 | 453-82 | 15% | | R206 | 1.0 |
| 41 | 453-83 | | 40% | (1:1) RG752/RG502 | N/A |
| 42 | 453-84 | | 40% | (2:1) RG752/RG502 | N/A |
| 43 | 453-85 | | 40% | (1:1) R203/RG502 | N/A |
| 44 | 453-86 | | 50% | R202H | 0.2 |
| 45 | 453-87 | | 50% | (1:1) RG752/RG502 | N/A |
| 46 | 453-88 | 10% | | (1:1) R203/R206 | N/A |
| 47 | 453-89 | 15% | | (1:1) R203/R206 | N/A |
| 48 | 453-90 | 10% | | (3:1) R203/R206 | N/A |
| 49 | 453-91 | 15% | | (3:1) R203/R206 | N/A |
| 50 | 453-92 | 10% | | R206 | 1.0 |
| 51 | 453-93 | 10% | | (2:1) R203/R206 | N/A |
| 52 | 453-94 | 15% | | (2:1) R203/R206 | N/A |

BT = Brimonidine Tartrate
BFB = Brimonidine Free Base
I.V. = Inherent Viscosity

Rod Formulations

Figure 2:
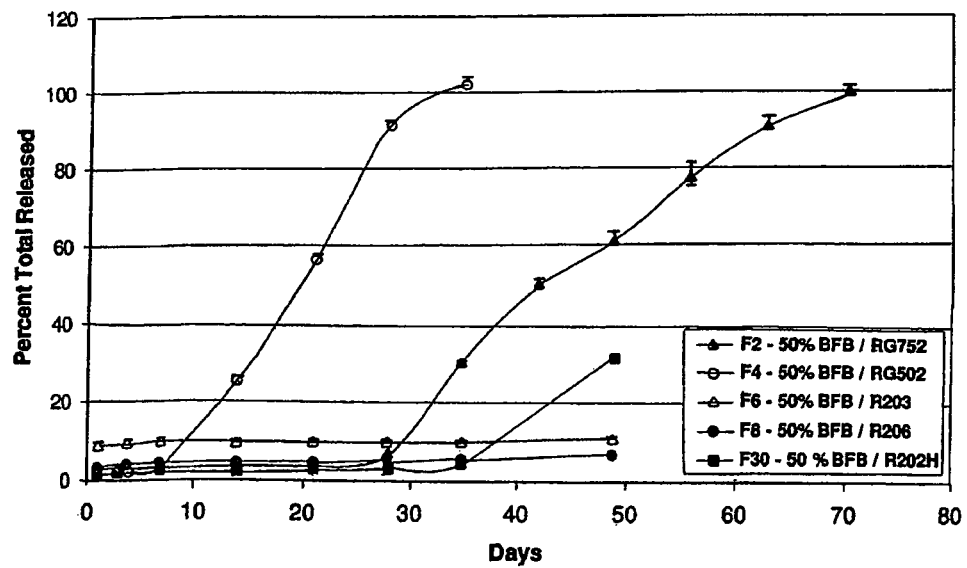
FIG. 2 is a graph similar to FIG. 1 showing the cumulative release profiles for biodegradable brimonidine free base containing implants with different combinations of biodegradable polymers.

The first 10 formulations were prepared with the five different polymers, RG752, RG502, R203, R206, and R202H each at 50% w/w drug load for both brimonidine tartrate and brimonidine free base. The release profiles are shown in FIG. 1 for brimonidine tartrate and FIG. 2 for brimonidine free base.

In most cases, formulations prepared with brimonidine tartrate had a faster initial burst than those prepared from brimonidine freebase using the same polymer, except for RG502. The data also show that brimonidine freebase had a lag time of approximately 30 days when formulated in poly (D, L-lactide) matrix (R203, R206, and R202H), while brimonidine tartrate was released completely on the first day (F5 and F7). This may be due to the quick dissolution of brimonidine tartrate on the surface of the implant.

Figure 3:
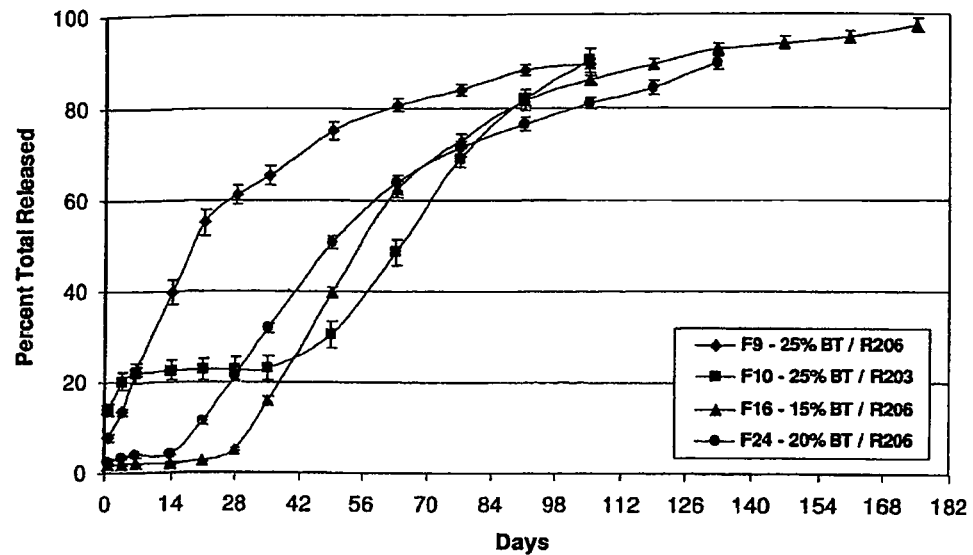
FIG. 3 is a graph similar to FIG. 1 showing the cumulative release profiles for biodegradable brimonidine tartrate containing implants having different concentrations of brimonidine tartrate.

Several formulations using R203 and R206 with drug doses lower than 50% were prepared, and the release profiles are shown in FIG. 3. Dramatic effects were observed when the drug load was lowered from 50% down to 25%. For example, formulation #9 was prepared with 25% brimonidine tartrate in R206 and it gave a total release of 89% after 105 days before leveling off. Comparing this to formulation #7, which was 50% brimonidine tartrate in R206, and it released 100% in one day. Similarly, formulation #10 was prepared with 25% brimonidine tartrate in R203 and it gave a total release of 90% after 105 days before it leveled off. Comparing this to formulation #5, which released 74% on day one.

With 20% brimonidine tartrate in R206 (F24), a 14 day lag time is present before it started releasing and eventually reaching 89.5% release after 134 days. At 15% brimonidine tartrate in R206 (F16), the lag time increased to 28 days before it started releasing and eventually reaching 97.6% after 175 days.

Figure 4:
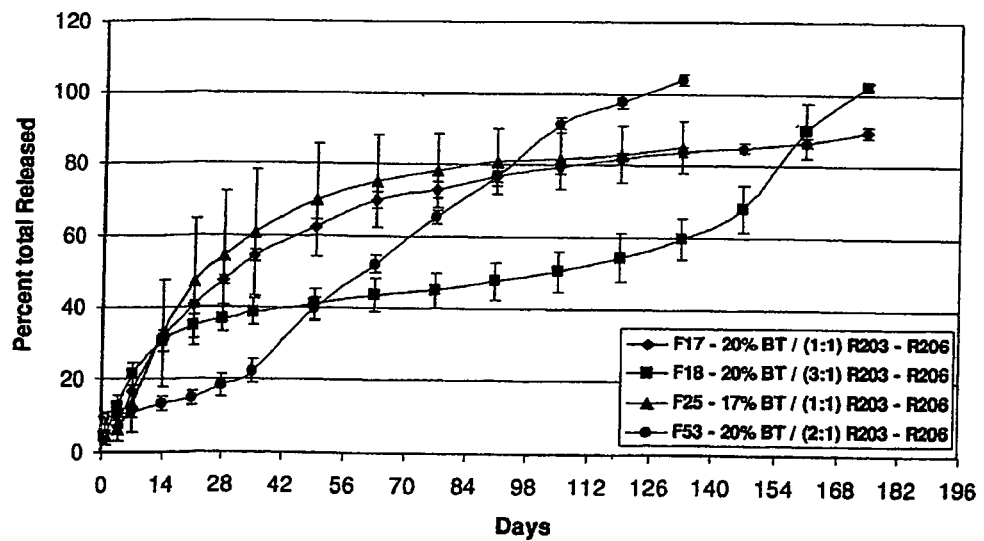
FIG. 4 is a graph similar to FIG. 3 showing the cumulative release profiles for biodegradable brimonidine tartrate containing implants having different concentrations of brimonidine tartrate and polymeric blends.

The release profiles of formulation #9 and #10 behaved in an opposite but complementary way, in that one polymer exhibits early release while the other exhibits a delayed release, but both reached the same end point at the same time. When both polymers were combined with a lower drug load, a more linear and longer release profile would be obtained, as shown in FIG. 4.

The data show that formulation #17, 20% brimonidine tartrate/(1:1) R203/R206, has a desirable in-vitro release profile for a six month release implant. It released approximately 90% of the brimonidine tartrate after 175 days. It was also shown that by varying the proportion of R203 and R206, even with the same drug load (Formulation #17, #18, and #53), different release profiles would result.

Figure 5:
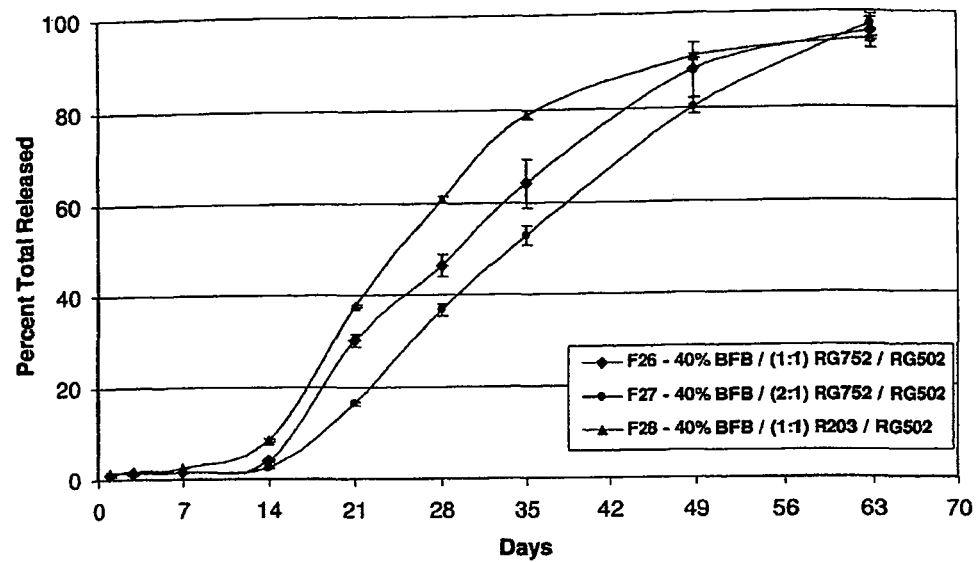
FIG. 5 is a graph similar to FIG. 4 showing the cumulative release profiles for biodegradable brimonidine free base containing implants having different concentrations of brimonidine tartrate and polymeric blends.

Brimonidine freebase formulations with polymer blends were also prepared to see if a more linear release profile could be obtained. Knowing its low solubility in aqueous media and its release characteristics in each polymer, different combinations of RG502-RG752, and RG502-R203 were prepared, and the release profiles are shown in FIG. 5.

The duration of release for all three formulations was approximately 2 months, but all three exhibited a lag time between 1 to 2 weeks. Two formulations (F32 and F33) were prepared with Purac polymer, PDLG (50/50)-Mw 9700, one with brimonidine tartrate and the one with brimonidine freebase. Both formulations had fast release with high standard of deviation; therefore, the release tests were stopped after 7 days.

Wafer Formulations

Figure 6:
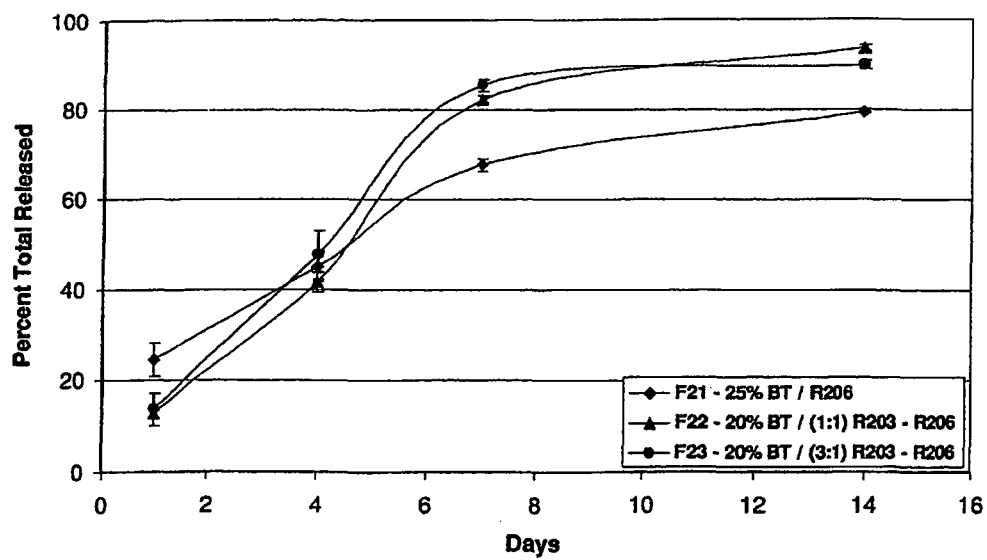
FIG. 6 is a graph showing the cumulative release profiles for brimonidine tartrate containing implants (wafers) having different concentrations of brimonidine tartrate and polymeric combinations.

The first set of wafer formulations was prepared from 3 existing rod formulations. Specifically, formulations #9, #17 and #18, with release reaching 89.4% after 105 days, 89.2% after 175 days, and 102% after 175 days, respectively. The release profiles of the first three wafer formulations are shown in FIG. 6.

Figure 7:
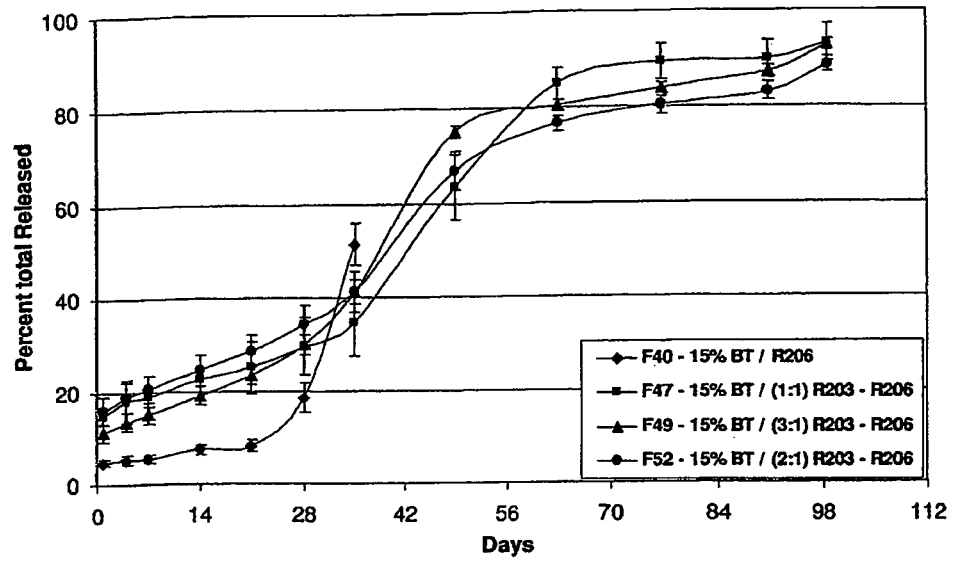
FIG. 7 is a graph similar to FIG. 6 showing the cumulative release profiles for biodegradable brimonidine free base containing implants having a different concentration of brimonidine tartrate and polymeric blends.
Figure 8:
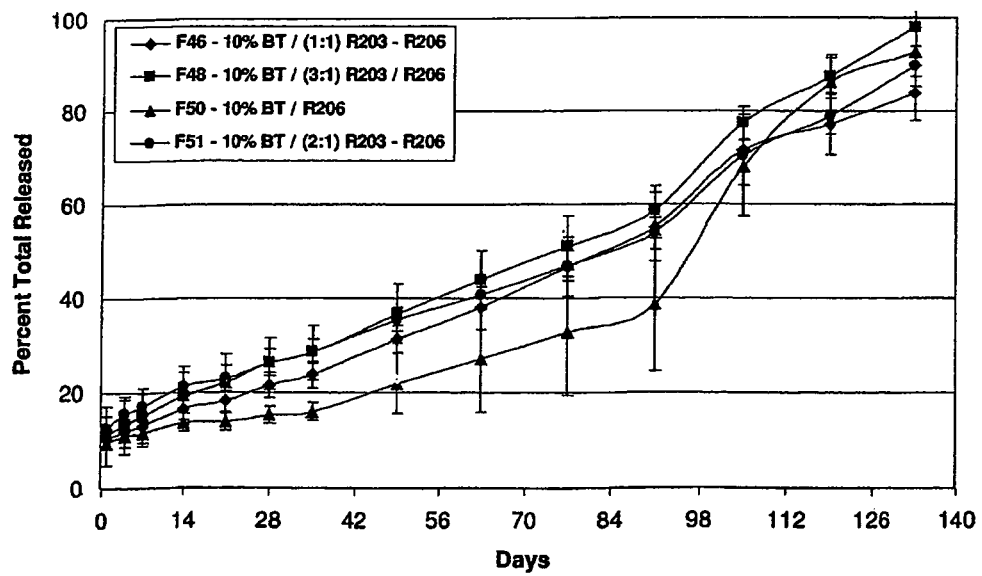
FIG. 8 is a graph similar to FIG. 4 showing the cumulative release profiles for biodegradable brimonidine free base containing implants having a different concentration of brimonidine tartrate and polymeric blends.

These three formulations had release periods lasting only two to three weeks, while their rod counterparts had release periods lasting three to four months. This may be due to the increased surface area of the wafer compared to that of a rod. In the wafer configuration, drug load also determines the duration of drug release. Therefore, drug load was reduced from 20-25% down to 15% and 10% and the release profiles are shown in FIGS. 7 and 8.

At 15% drug load, formulation #7 had a cumulative release 51.4% after 35 days, while formulation #47, 49, and 52 had cumulative releases of 93.2%, 92.8% and 88.5%, respectively, after 99 days. The latter three formulations may be effective as a 4-month drug delivery system.

At 10% drug load, formulations #46, #48, #50, and #51 had cumulative releases of 83.8%, 98.0%, 92.7% and 89.2%, respectively, after 133 days. These four formulations may be effective as 5-month drug delivery systems. Both FIGS. 7 and 8 demonstrate that lowering the drug load yielded not only a longer duration of release but also more linear release profiles for all formulations. The figures also show that using a polymer blend instead of just a single polymer, such as R206, should yield a more linear release profile with lower standard of deviations.

Figure 9:
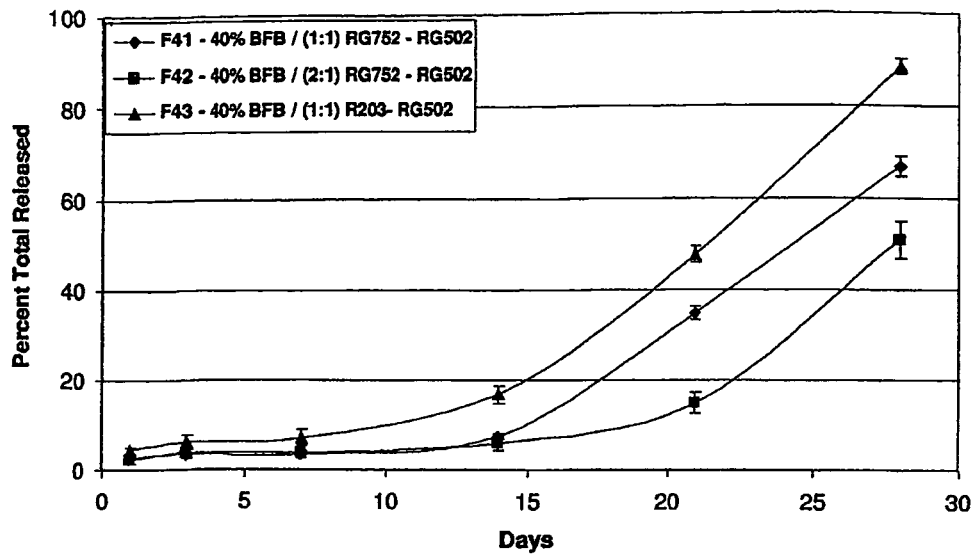
FIG. 9 is a graph similar to FIG. 5 showing the cumulative release profiles for biodegradable brimonidine free base containing wafer implants.

Three wafer formulations were prepared from three previous rod formulations #26, #27, and #28, and the release profiles are shown in FIG. 9. The three wafer formulations released slightly faster than their rod counterparts at day 28 and they were expected to complete their release between days 31 to 55.

Conclusions

Of the 15 rod formulations prepared from brimonidine tartrate, three formulations had release periods longer than 3 months (F9, F10, and F53), two formulations had release periods longer than 4 months (F24 and F25), and three formulations had release periods close to 6 months (F16, F17, and F18). Of the 8 rod formulations prepared from brimonidine freebase, 3 had release periods longer than 2 months (F26, F27, and F28).

Of the 22 wafer formulations, 11 were prepared from brimonidine tartrate and 11 were prepared from brimonidine freebase. Of the 11 wafer formulations prepared from brimonidine tartrate, 3 had release periods of about 4 months (F47, F49, and F52), and 4 had release periods between 4 and 5 months (F46, F48, F50, and F51). Of the 11 wafer formulations prepared from brimonidine freebase, 4 had release periods between 3 and 4 months (F35, F36, F38, and F39), and 5 had release periods between one to two months (F34, F37, F41, F42, and F43).

In general, the wafer formulations prepared from brimonidine tartrate or brimonidine freebase have faster release than their rod counterparts.

Example 2

In Vivo Testing of Intraocular Implants Containing Brimonidine and a Biodegradable Polymer Matrix Cynomolgus monkeys were randomly assigned to receive either placebo (n=2) or brimonidine (n=2) formulated intravitreal implants. Baseline measures were performed 3 days prior to implantation and 10 days following implantation with intraocular pressure (IOP), mfERG, laser Doppler scanning topography/flowmetry (HRT/HRF), optical coherence tomography (OCT), indocyanine green angiography (ICG) and fluorescein angiography (FA).

Three implants (Formulation #17 described in Example 1), each formulated with 200 µg brimonidine or placebo were implanted intravitreally into an eye through a port made with an MVR blade (OS), the port was closed with sutures. Wide angle contact lens fundus photography verified implant count and localization.

Branch retinal vein occlusion (BRVO) was achieved by injecting 1 ml of 20 mg/kg Rose Bengal intravenously followed by thermal irradiation using Omni Coherent Diode laser at 532 nm, 600 mW, 50 um spot size, 0.01 sec pulse mode with a 1.6× inversion contact lens. Laser pulses were delivered until the vein segment was closed. One brimonidine treated monkey received 235 pulses and the other received 78 pulses. One placebo treated monkey received 43 pulses and the other received 31 pulses. Vascular occlusion of a vein was induced in the superior arcade approximately one disc diameter from the optic nerve head. Occlusion was verified post-laser by fundus photography.

Funduscopic observations at day 1 following BRVO showed dramatic retinopathy and vasculopathy in both monkeys with placebo implant—marked retinal edema and dot blot hemorrhages, vessel tortuosity, cotton wool spots. Fluorescein angiography verified vein occlusion and stagnate blood flow upstream from the lasered region and elucidated late phase fluorescein leak and pooling from retina capillaries. Monkeys with brimonidine implants had less than 5 small dot blot hemorrhages, some retinal edema localized to the superior retina. Fluorescein angiography in brimonidine monkeys showed reperfusion of the once occluded vein with minimal stagnate blood flow.

Figure 10:
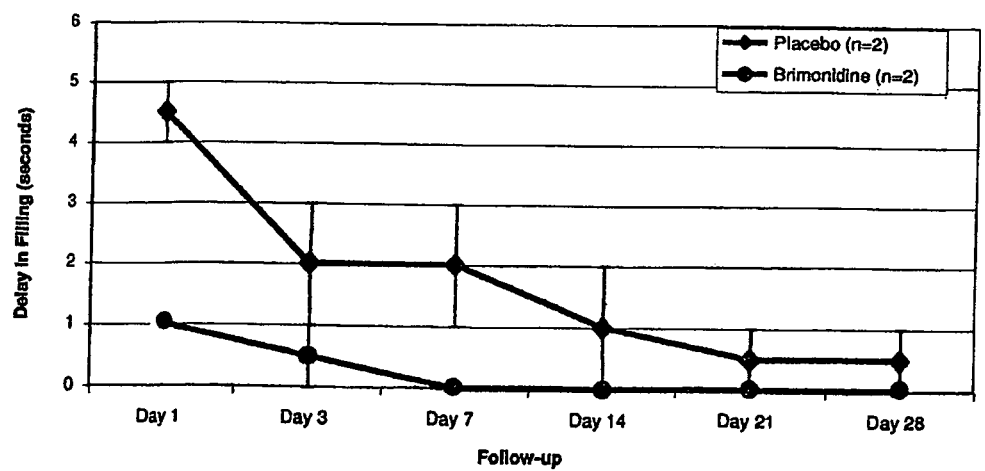
FIG. 10 is a graph showing the delay in filling of sodium fluorescein during angiography following branch retinal vein occlusion (BRVO) versus time in monkeys that have received brimonidine tartrate containing biodegradable implants or placebo implants.

The brimonidine containing implants decreased the duration of vascular occlusion as shown in FIG. 10. Delay in fluorescein filling of the occluded vein was quantified using Metamorph 6.0 software. Intensity measurements were made with pre-defined regions of interest for early and late phases of fluorescein angiography to quantify delay in filling and the observed delay in fluorescein clearance. The delay in early phase filling of fluorescein (seconds) in the occluded vein from baseline fluorescein angiography filling is illustrated in FIG. 10.

Figure 11:
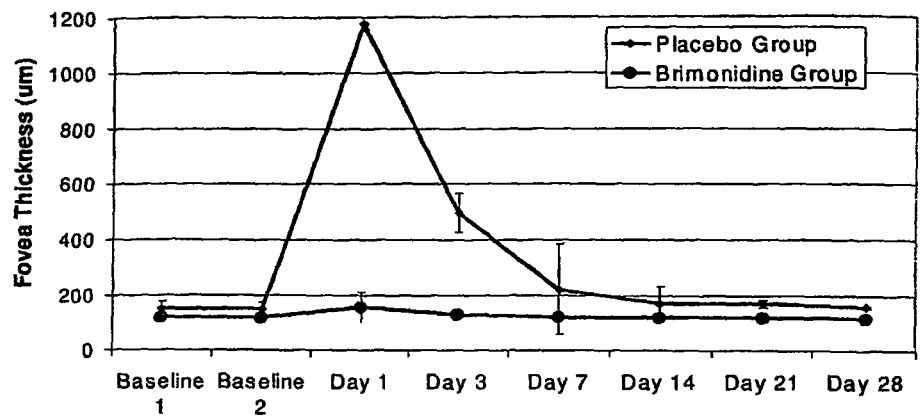
FIG. 11 is a graph of foveal thickness as a function of time in monkeys that have received brimonidine tartrate containing biodegradable implants or placebo implants and experienced BRVO.

Fovea thickness measurements from OCT single line scans (6 mm) show an increase in retinal edema as a result of vascular occlusion in the placebo group. Brimonidine containing implants decreased the magnitude of retinal edema associated with vascular occlusion. A series of line scans (covering 3 mm²) directly compare changes in retinal thickness in the superior region surrounding the occluded vein with thickness changes in the inferior retina. Retinal edema in placebo monkeys was so profound that fluid accumulation occurred in the inferior region of the retina. In contrast, the brimonidine group did not have a significant change in inferior retina edema compared to baseline, as shown in FIG. 11.

Figure 12:
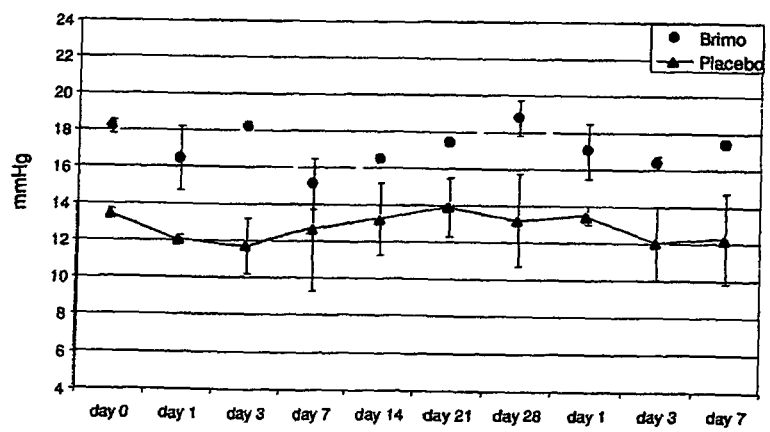
FIG. 12 is a graph of intraocular pressure as a function of time in monkeys that have received brimonidine tartrate containing biodegradable implants or placebo implants and experienced BRVO.

Intraocular pressure (IOP) was recorded (OD and OS) in each group in triplicate post implantation and prior to all follow-up electrophysiology and retinal imaging procedures. The brimonidine implants did not significantly lower IOP in eyes prior to or during BRVO, as shown in FIG. 12.

Figure 13:
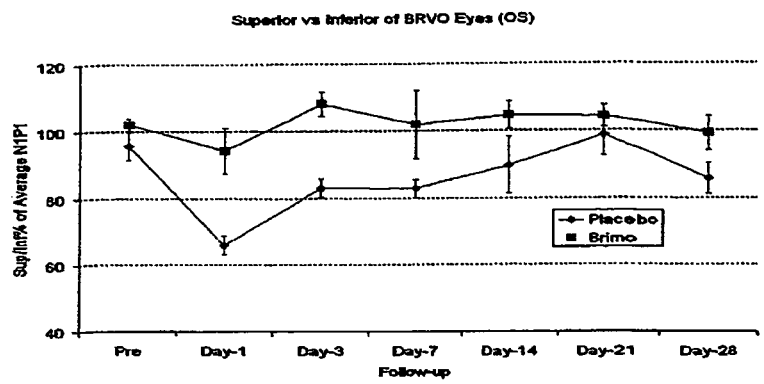
FIG. 13 is a graph of the superior/inferior percent response to a multifocal ERG as a function of time in monkeys that have received brimonidine tartrate containing biodegradable implants or placebo implants and experienced BRVO.

Multi-focal ERG was performed using a VERIS 5.0 system. A stimulus field of 241 hexagons was positioned to record superior retina and central retina foveal response. In the placebo group, foveal responses were absent through 3-4 weeks post BRVO induction, whereas, the foveal response in the brimonidine group was slightly lower but pronounced at day 1 following BRVO, with recovery and/or higher foveal response for the remainder of the study. The graph in FIG. 13 shows the superior/inferior % response for both groups. BRVO in monkeys treated with placebo have less responsive retinal function with a trend toward recovery late in the study versus relatively consistent retinal function with brimonidine implants.

Figure 14:
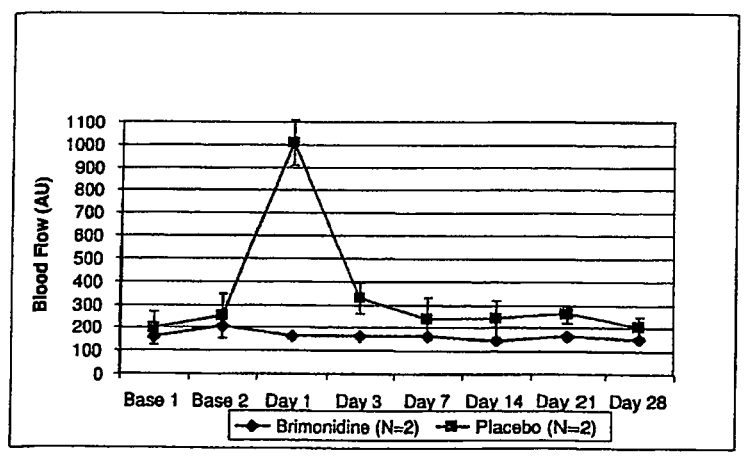
FIG. 14 is a graph of blood flow as a function of time in monkeys that have received brimonidine tartrate containing biodegradable implants or placebo implants and experienced BRVO.

Laser Doppler Flowmetry (HRF) was used to measure blood flow in the fovea, superior and inferior retina regions. The graph of FIG. 14 shows the results from blood flow measurements acquired with a 10-20 degree zone, centered at the fovea. Blood flow in the fovea appears to be unchanged in the brimonidine group following BRVO, but is sharply elevated at day 1 post BRVO in the placebo group.

Intravitreal application of three brimonidine intraocular implants has lessened the magnitude and duration of localized vascular occlusion and associated vasculopathy and retinopathy in monkeys.

In addition, the amount of laser burns needed to close the veins was higher in the brimonidine group compared to placebo (brimonidine: 157±79, n=2; placebo: 37±6, n=2). Together, these data show that the presence of brimonidine increases the difficulty of occluding retinal vasculature and decreases the duration of that occlusion.

Example 3

Treatment of Glaucoma with an Intraocular Implant Containing Brimonidine Associated with a Biodegradable Polymer Matrix A 68 year old female complains to her physician that it is becoming difficult to see. The physician determines that she has elevated intraocular pressure levels, and diagnoses her with glaucoma. An implant containing 200 µg of brimonidine tartrate and 800 µg of a combination of biodegradable polymers (R203 and R206 at a 1:1 ratio, as described above in Example 1) is placed in the vitreous of both of the woman's eyes using a trocar. After about 2 days, the woman begins to notice a change in her eyes, presumably due to a decrease in intraocular pressure. The loss of vision is prevented for about five months after the implant procedure.

Example 4

Treatment of Ocular Conditions with Various Active Agents

An implant can be formulated with various active agents, including the agents described herein, following the procedures in the Examples above. These implants can provide an extended therapeutic treatment of an ocular condition, that is a therapeutic effect during a period of time during release of the active agent or after release of all of the active agent from the implant and during which there is no longer a therapeutic amount of the active agent present at the ocular site at which the implant was placed. Thus, an implant can be prepared containing an alpha-2 adrenergic receptor agonist, such as clonidine, apraclonidine, or brimonidine (available from Allergan, Irvine, Calif. as brimonidine tartrate ophthalmic solution, under the tradename Alphagan-P®). Thus, for example, a brimonidine extended therapeutic treatment implant can be implanted into an ocular site (i.e. into the vitreous) of a patient with an ocular condition for a desired extended therapeutic effect. The implant may contain from about 50 µg to about 500 µg of Alphagan or Alphagan-P depending on the size of the implant. The brimonidine extended therapeutic treatment implant can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using the procedure such as trocar implantation. The implant can release a therapeutic amount of the active agent to provide and retain a therapeutic effect for an extended period of time to thereby treat a symptom of an ocular condition. For example, the implant may be effective to improve visual acuity, visual contract sensitivity, or both.

Example 5

Use of Intraocular Alpha-2 Adrenergic Receptor Agonists Implants to Enhance, Restore and/or Improve Visual Acuity Experiments were carried out with intraocular implants in mammalian eyes. Thus, degradable polymer implants containing as active agent an intraocular alpha-2 adrenergic receptor agonist were placed in the vitreous of both normal and damaged or diseased (model system) rabbit eyes. The results of the experiments showed that an intraocular alpha-2 adrenergic receptor agonist implant can: (1) enhance visual acuity in normal eyes, and; (2) restore visual acuity in diseased or damaged eyes.

Formulation #17 of Example 1 was used in these Example 5 experiments. Thus, the implants used comprised the alpha-2 agonist brimonidine tartrate formulated as a solid, biodegradable rod (weighing about 1 mg) to form a sustained release drug delivery device (i.e. an implant). The implant consisted of 200 µg brimonidine tartrate and 800 µg of a poly-lactide co-polymer mixture of resomers R203 and R206 in a 1:1 weight ratio. The placebo implant was a 1 mg rod implant made of a poly-lactide co-polymer mixture of resomers R203 and R206 in a 1:1 weight ratio.

When the implant was administered intravitreally in rabbits we found that enhanced or normalized visual acuity resulted. Visual acuity was measured as a sweep visual evoked potential threshold. Improved visual acuity was measured in each of three different ocular conditions:

1) in normal rabbit eyes;
2) in VEGF damaged rabbit eyes. These rabbit eyes were treated intravitreally with 500 ng of VEGF to induce optic nerve head swelling, retinal vessel leak, dilation and tortuosity, to thereby simulate disease aspects common to ocular conditions such as macular edema, optic nerve head edema, diabetic retinopathy, and neovascularization, and;
3) in rabbit eyes with outer retina injury induced by a transient ischemic event with elevated IOP 8 months prior to use of the implant.

Significantly: (a) in ocular condition 2) above, the implant improved visual acuity without reducing the vasculopathy (tortuosity, leak, dilation) associated with the VEGF treatment, and; (b) in ocular condition 3) above, the implant improved visual acuity without changing the clinical appearance of the retina in these ischemic damage eyes, as assessed by color fundus photography. This indicates that the alpha 2 agonist active agent released by the implant caused an augmentation of the tonic activity of the functioning retinal neuronal cells that remained following the induced injury or disease state in ocular conditions 2) and 3). It can be hypothesized that the remaining normal cells functioned better to compensate for and to improve vision even though the disease state was still present.

Procedure for Inducing Retinal Ischemic Injury.

Rabbits were anesthetized with isofluorane, and prepared for unilateral acute retinal ischemia by raising IOP in the OD eye by 120 mm Hg for 45 minutes. To accomplish this, a reservoir with PBS was suspended 65 inches above the eye and connected to a 30 gauge needle inserted through the cornea into the anterior chamber. A drop of topical anesthetic (proparacaine) was placed upon the cornea prior to needle insertion. And, a drop of anti-inflammatory agent (Pred-G) was placed onto the cornea immediately following needle removal.

Procedure for Measuring Visual Acuity.

Visual acuity was measured in conscious rabbits using sweep visual evoked potential (swVEP). swVEP is an electrophysiological technique for assessing visual acuity typically used young children who can not read the Snellen eye charts. Pattern reversal images of increasing spatial frequency are projected onto the macula while simultaneously recording electrical activity (VEP) from the scalp. Images with lower spatial frequency generate large signals which get smaller as the spatial frequency increases, until signal=noise; this threshold is the visual acuity. The procedure in rabbits requires first implanting permanent electrodes on the scalp to enhance signal strength and allow recording for the same position from follow-up visits. After two-weeks to allow for healing, the visual acuity measurements can be made.

Rabbits were anesthetized with ketamine and xylazine for the implantation procedure. The scalp was aseptically prepared and implanted with four stainless steel screws (#0-80× ⅜). Two active electrodes were placed at 6 mm on either side of the midline, 6 mm above bregma; 1 ground electrode was placed at midline, 6 mm above the active electrodes; and, 1 reference electrode was placed at midline, 6 mm above the grounding electrode.

For the acuity test, eyes were fully dilated with 1% tropicamide and 10% phenylephrine. The rabbits were placed in stainless steel restrainers that allowed projection of the pattern-reversal images onto the visual streak. The rabbits were fully-conscious. Images were projected via a specially-designed fundus camera stimulator under control of the Power-Diva software version 1.8.5. Each rabbit was placed so that it's eye was located at 50 mm in front of camera which is equivalent to 50 cm from a 21 in CRT monitor. Recording electrodes were connected to Grass Neurodata Acquisition System (Model 12CA) with the following specifications:
Channel 1 for OD eye and Channel 2 for OS eye.
Filter range between 3 to 100 Hz.
Amplification: 50 K
Line frequency filter=OFF.

Vertical steady-state pattern-reversal sweep stimulus at spatial frequency range of 0.1 to 5 cycles per degree at a temporal frequency of 7.5 Hz were applied to the eye at mean luminance of 600 cd/m$^2$ and contrast of 80%. Five to 40 trials, 10 secs each, were collected from each eye. The number of trials was based on the signal-to-noise ratio. Trials were averaged and the threshold (visual acuity) was determined by software or manual fitting at signal-to-noise ration no less than 2.5. Threshold values were then normalized by expressing as a percent of the contralateral eye.

The effect on visual acuity of the brimonidine implant vs placebo was studied in three different conditions on six different group of rabbit eyes, as explained below. For each of the three groups of rabbits the implants were placed in the vitreous using The implants are inserted into the vitreous using the applicator (with a 22 gauge needle) set forth in U.S. patent application Ser. No. 11/021,947, filed Dec. 23, 2004.

(A) In the first study two groups of rabbits with normal (untreated) eyes were used. One brimonidine implant was intravitreally implanted into each left eye of each rabbit of group 1 (N=7). One placebo implant was intravitreally implant into the left eye of each rabbit of group 2 (N=7) using the same procedure. The right eye of each rabbit in both groups 1 and 2 was not treated and served as controls to normalize the data obtained. Visual acuity was measured in both eyes of the rabbits in both groups and is set forth in FIG. 15 as a percent of the visual acuity of the contralateral (right) normal eye.

Figure 15:
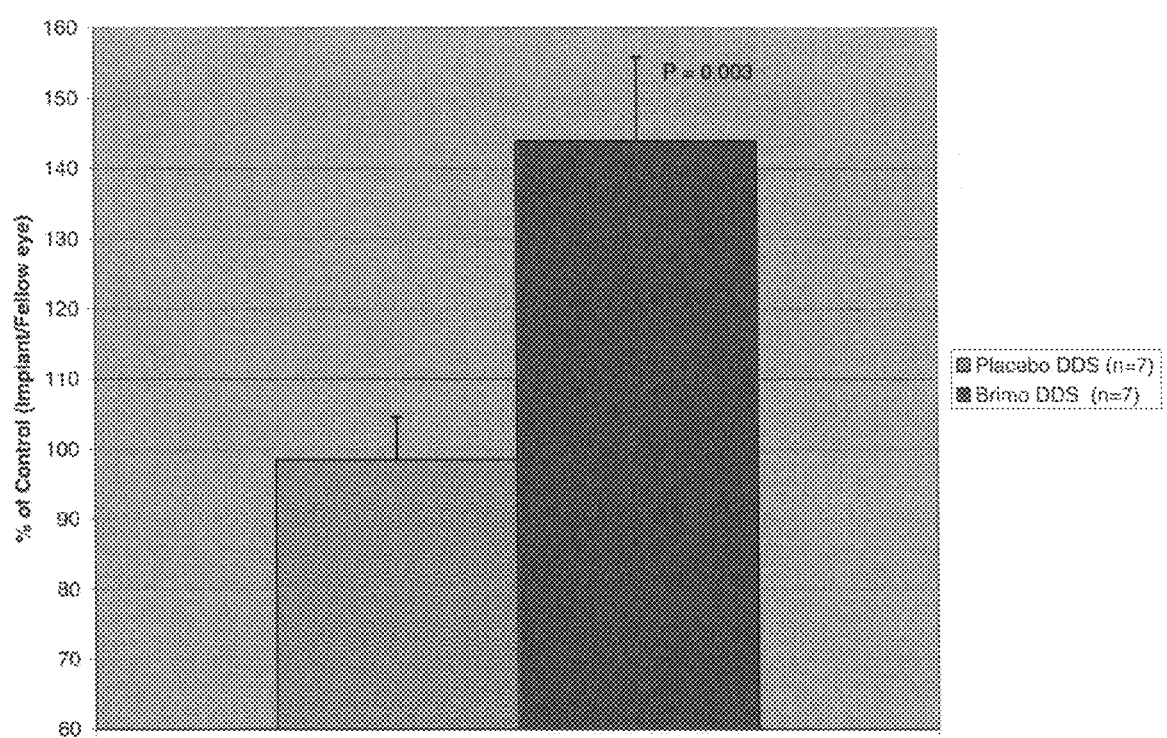
FIG. 15 is a bar graph showing the effect upon visual acuity (as a percent of the visual acuity of the untreated [control] left eye) (Y-axis) in normal rabbit right eyes two weeks after intravitreal administration of either a brimonidine implant or a placebo implant (X-axis).

FIG. 15 shows the effect of the brimonidine implant and of the placebo implant on visual acuity in normal eyes of rabbits. The FIG. 15 results were recorded two weeks after implantation of either the brimonidine implant or the placebo implant and show that the placebo implant did not cause a significant visual acuity change. Thus, the placebo implant caused visual acuity to change only by 1.5%±6%. However, use of the brimonidine implant clearly caused a significant enhancement of visual acuity in normal rabbit eyes. Thus, the brimonidine implant caused visual acuity to improve by 44%±12% (up to a 56% vision improvement in a normal eye). A comparison of the responses to the placebo implant and to the brimonidine implant with an unpaired Student's 'T' test show statistical difference with a p value of 0.003.

(B) In the second study two groups of rabbits eyes were used. One brimonidine implant was intravitreally implanted into each left eye of each rabbit of group 1 (N=7). One placebo implant was intravitreally implant into the left eye of each rabbit of group 2 (N=7) using the same pars plana insertion procedure. The right eye of each rabbit in both groups 1 and 2 was not treated and served as controls to normalize the data obtained. Two weeks after implantation each implanted eye was intravitreally administered 500 ng of vascular endothelial factor (VEGF) (obtained from R&D Systems as product number 293-VE-50) as a 50 μl bolus. Visual acuity was measured in both eyes of the rabbits in both groups and is set forth in FIG. 16 as a percent of the visual acuity of the contralateral (right) eye.

Figure 16:
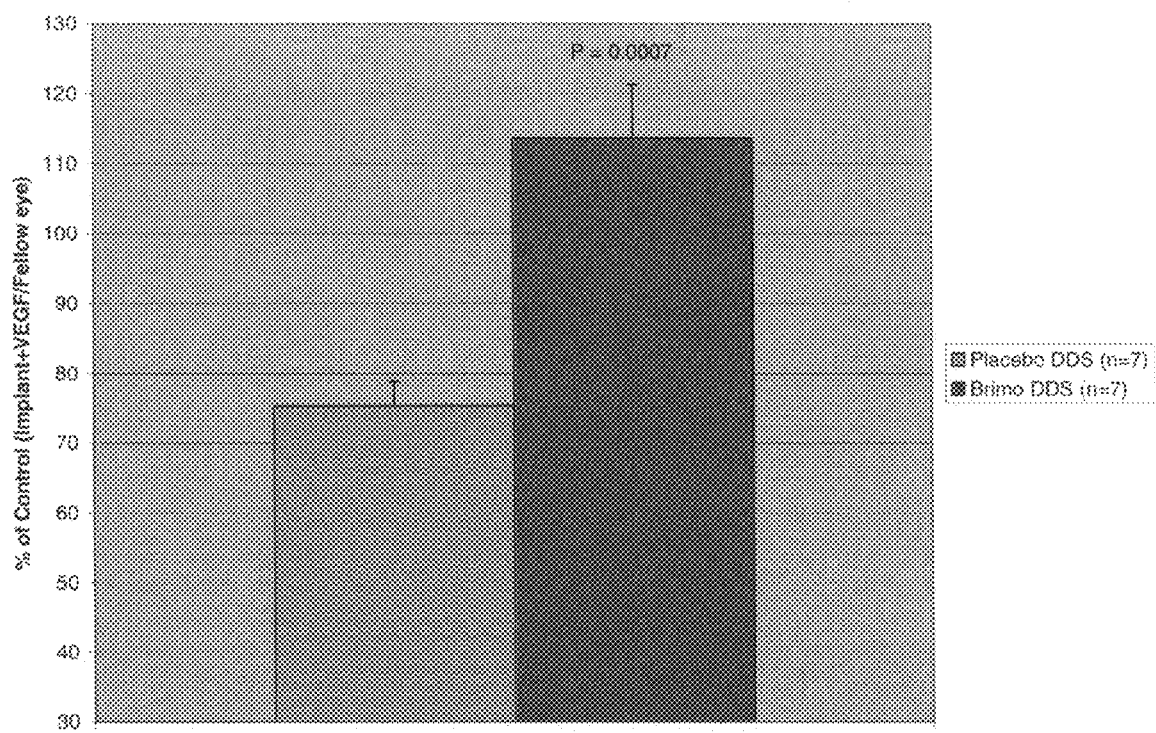
FIG. 16 is a bar graph showing the effect upon visual acuity (as a percent of the visual acuity of the untreated [control] left eye) (Y-axis) three weeks after intravitreal administration of either a brimonidine implant or of a placebo implant in the right eyes and one week after VEGF induced injury of the same right eyes (X-axis).

FIG. 16 shows the effect of the brimonidine implant and of the placebo implant on visual acuity in the VEGF treated rabbit eyes. The FIG. 16 results were recorded three weeks after implantation of either the brimonidine implant or the placebo implant and one week after VEGF administration. The FIG. 16 results show that the placebo implant, VEGF treated eyes had a visual acuity deficit of about 25%±4%. The FIG. 16 results also show that the brimonidine implant, VEGF treated eyes had a visual acuity improvement of about 14%±8% (up to 22% vision improvement in an eye with a vasculopathy). Thus, use of the brimonidine implant normalized visual acuity in eyes treated with VEGF despite the presence of vasculopathy. The brimonidine implant did not reduce the vasculopathy induced by VEGF, but did reduce the neurosensory retina deficit induced by the VEGF treatment. A comparison of the responses to the placebo implant and to the brimonidine implant with an unpaired Student's 'T' test showed statistical difference with a p value of 0.0007.

(C) In the third study two groups of rabbits' eyes were used. One brimonidine implant was intravitreally implanted into each left eye of each rabbit of group 1 (N=5). One placebo implant was intravitreally implant into the left eye of each rabbit of group 2 (N=5) using the same procedure. The right eye of each rabbit in both groups 1 and 2 was not treated and served as controls to normalize the data obtained. At day zero ischemic injury was induced in the left eye of each rabbit in both groups. Thirty two weeks later each ischemic injury left eye of each rabbit in group 1 was implanted with the placebo implant and each left eye of each ischemic injury left eye of each rabbit in group 2 was implanted with the brimonidine implant. At week forty four visual acuity was measured in both eyes of the rabbits in both groups and is set forth in FIG. 17 as a percent of the of the visual acuity of the contralateral normal or untreated (right) eye.

Figure 17:
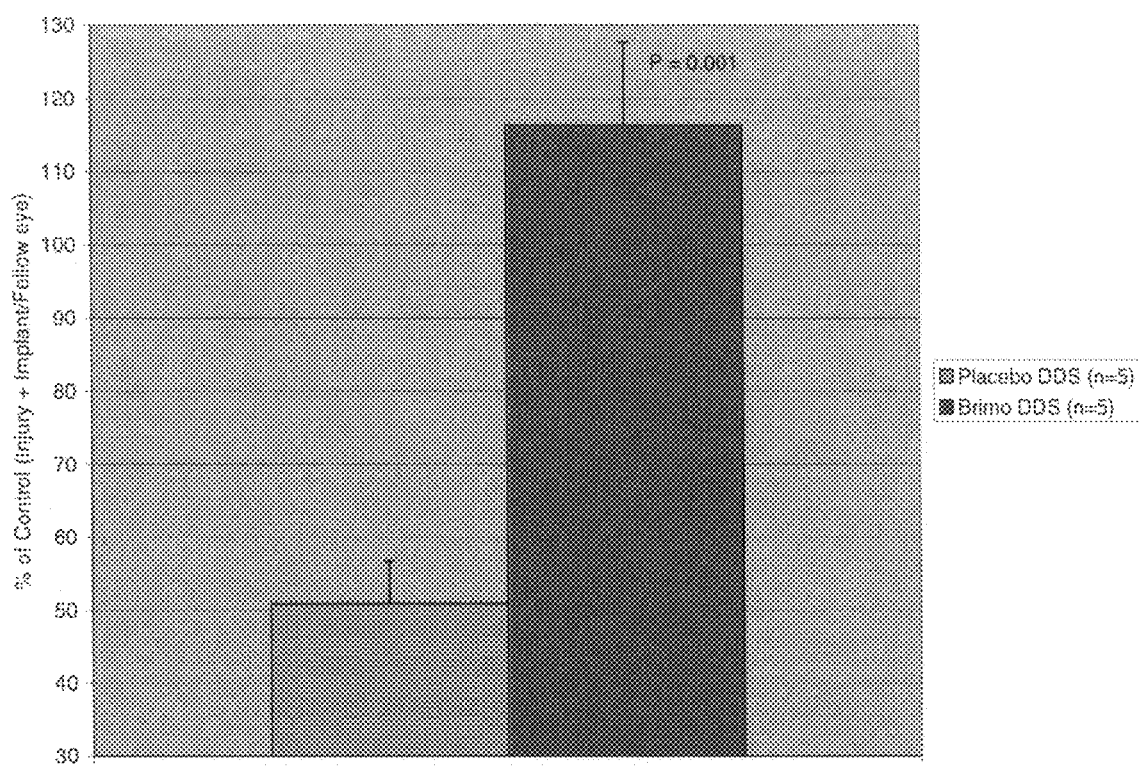
FIG. 17 is a bar graph showing the effect upon visual acuity (as a percent of the visual acuity of the untreated [control] right eye) (Y-axis) twelve weeks after intravitreal administration of either a brimonidine implant or of a placebo implant in the right eyes and eleven months after induced ischemic injury of the same right eyes (X-axis).

FIG. 17 shows the effect of the brimonidine implant and of the placebo implant on visual acuity in eyes of rabbits with existing injury from an ischemic event. Histology shows that this procedure results in outer retina injury to photoreceptors, the RPE and associated tissues. Rabbits with a visual acuity deficit in the left resulting from the transient ischemic procedure were randomized into two groups. Data are expressed as a percent of the contralateral normal eye. The FIG. 17 results were recorded twelve weeks after implantation with either the brimonidine implant or the placebo implant and eleven months after the induced ischemic event to each implanted eye. The FIG. 17 results show that the placebo implant, ischemic injury eyes has a visual acuity decrease of 37%±8%. The FIG. 17 results also show that the brimonidine implant, ischemic injury eye had a visual acuity improvement of 14%±9%. Thus, use of the brimonidine implant restored or improved visual acuity in rabbit eyes with an outer retina (induced ischemic) injury. A comparison of the responses to the placebo implant and the brimonidine implant with an unpaired Student's 'T' test showed a statistical difference with a p value of 0.001.

These experiments showed that a locally (i.e. intravitreally) administered alpha-2 adrenergic receptor agonist can be used to improve vision (enhance visual acuity) in normal eyes. These experiments also showed that a locally (i.e. intravitreally) administered alpha-2 adrenergic receptor agonist can be used to improve, repair or restore vision in eyes with an ocular condition such as an inflammatory, neovascular, tumor, vascular occlusive, and/or optic nerve disease or condition, including glaucoma.

A separate group of rabbits were studied to obtain pharmacokinetic data. In these rabbits the implants were inserted using a surgical intravitreal implantation procedure performed as follows: a conjunctival incision was made, and a sclerotomy was performed with a 20-gauge MVR blade. The sclerotomy was 3 mm from the limbus and lateral to the dorsal rectus muscle between the 10 and 12 o'clock positions on the right eye, and between the 12 and 2 o'clock positions on the left eye. Using a sterile forceps, the test article was inserted through the sclerotomy. The sclerotomy was closed with 9-0 Prolene suture material. A sterile ocular lubricant was applied to the eye following the implantation procedure. Blood was collected from rabbits prior to euthanasia/necropsy on Days 8, 31, 58, 91, 136, or 184. The aqueous humor, vitreous humor, lens, retina and plasma samples from the rabbits were analyzed by using liquid chromatography-mass spectrometry/mass spectrometry (LC-MS/MS) methods.

Table 3 shows the data obtained in this pharmacokinetic study. Intraocular brimonidine concentrations in the aqueous humor, iris-ciliary body, lens, retina, vitreous humor and plasma concentrations at various times ("Days" in the left hand side column of Table 3) after intravitreal (into the mid-vitreous) implantation of the 200 µg brimonidine implant (Formulation #17) in albino rabbit eyes was measured. As shown by Table 3, after intravitreal implantation of the Formulation #17 brimonidine implant:

1. brimonidine was not detectable at any time point in the aqueous humor of the rabbit eyes implanted with the brimonidine implant;

2. the brimonidine had a posterior clearance as opposed to an anterior clearance after release from the intravitreal implant, as shown by the higher retinal concentration;

3 detectable levels of brimonidine were released from the implant into the vitreous over at least a ninety day period;

4. therapeutic levels of the brimonidine existed in the retina for about twice as long at the implant released brimonidine from the implant: brimonidine was present in the retina for at least 84 days, although all the brimonidine had been released from the implant after about 91 to about 120 days;

5. the implant allowed an intra-retinal depot of brimonidine to be formed.

TABLE 3

| | Intraocular brimonidine concentrations | | | | | |
|---|---|---|---|---|---|---|
| Day | Aqueous humor (ng/mL) | Iris-ciliary body (ng/g) | Lens (ng/g) | Retina (ng/g) | Vitreous humor (ng/mL) | Plasma (ng/mL) |
| 8 | NC | 942 (3010)[d] | 45.1 ± 13.4 | 3630 ± 2111 | 47.2 ± 13.1 | 0.092 (0, 0.184) |
| 31 | NC | 25.9 ± 9.11 | 17.0 ± 3.92 | 35.3 ± 15.5 | 9.35 ± 6.25[b] | 0.0575 (0, 0.115) |
| 58 | NC | 69.4 ± 55.3 | 17.9 ± 12.5[b] | 122 ± 57.3[a] | 5.6 ± 3.24[b] | 0.255 (0.208, 0.302) |
| 91 | NC | 42.9 ± 18.7[c] | 50.1 ± 14.8 | 488 ± 471[b] | 59.3 ± 43.2 | NC |

TABLE 3-continued

Intraocular brimonidine concentrations

| Day | Aqueous humor (ng/mL) | Iris-ciliary body (ng/g) | Lens (ng/g) | Retina (ng/g) | Vitreous humor (ng/mL) | Plasma (ng/mL) |
|---|---|---|---|---|---|---|
| 136 | NC | 107 ± 41.5 | 16.2 ± 12.3$^a$ | 22.6 ± 5.9 | NC | NC |
| 184 | NC | NC | 1.18 ± 0.71$^b$ | 59.8 ± 35.0$^b$ | NC | NC |

NC, not calculable because >50% of concentrations contributing to mean were BLQ (below limit of quantification).
Data expressed as mean ± SEM (N = 4 eyes and N = 2 plasma per sampling time).
BLQ = Below limit of quantitation (aqueous and vitreous humor: <10 ng/mL; lens, retina and iris-ciliary body: <0.5 ng; plasma: <0.05 ng/mL).
$^a$N = 4. One sample was BLQ (included in the mean calculation as zero).
$^b$N = 4. Two samples were BLQ (included in the mean calculation as zero).
$^c$N = 3. One sample was not determined (not included in the mean calculation).
$^d$N = 2. Two samples were ALQ (above limit of quantification) (estimated mean value in parentheses).

To conclude, our results show that an alpha-2 agonist (non-selective or receptor subtype selective) intravitreal implant can be used to enhance, repair, restore or improve visual acuity in mammalian eyes.

Significantly, our experiments showed that an intravitreal brimonidine implant can be used to improve visual acuity in both normal eyes and in diseased eyes. The results presented herein show that in VEGF treated eyes show that the implant can be used as a prophylactic to prevent a future vision loss. The results presented herein in damaged/diseased (i.e. ischemic) eyes show that an implant can be used to improve visual acuity in an eye without remission or disappearance of the eye damage/disease. That is, the implant appears to cause the remaining normal retinal cells to function better to compensate and improve vision, even though the eye damage/disease has not been reduced as to it's physical extent in the retina.

Implants within the scope of our invention can be used:

1. as a prophylaxis to mitigate against impending retinal neurosensory dysfunction in a variety of ocular conditions, including retinal disorders in patients that have a predisposition to or risk factors associated with a retinal disorder.

2. as a therapeutic (alone or in combination with one or more additional active agents) to treat posterior ocular conditions, such as retinal diseases associated with degeneration of the retina, such as a macula degeneration (such as an age related macular degeneration), an ocular edema, such as a macular edema, a vascular occlusive condition, an optic or retinal neuropathy, and/or a retinal tumor. For example, an implant can be made comprising an alpha 2 agonist to lower IOP and/or to improve visual acuity and a steroid (such as dexamethasone or triamcinolone) to reduce inflammation.

3. as a therapeutic (alone or in combination with one or more additional active agents) useful in retinal diseases and disorders with detachment of the retina.

4. as a therapeutic (alone or in combination with one or more additional active agents) useful in surgical retinal procedures that require vitrectomies and manipulation that can have a negative impact of the retina.

5. as a therapeutic (alone or in combination with one or more additional active agents) to treat retinal diseases that have a nutritional deficiency, such as a vitamin A deficiency.

6. as a therapeutic (alone or in combination with one or more additional active agents) to treat retinal injury from accidental light exposure, such an operating microscope light or industrial lasers.

7. as an adjunct with steroids for treating retinal diseases, where steroids are used to reduce ocular inflammation and macular or optic nerve edema.

8. as an adjunct to photodynamic therapy (PDT) where PDT is used to treat retinal conditions associated with leakage from retinal and related tissue vessels.

9. as an adjunct to other types of electromagnetic radiation such as laser photocoagulation used to treat macula edema or neovascularization, and transpupillary thermal therapy (TTT) that is used to treat choroidal neovascularization (CNV).

10. as an adjunct to radiation therapy or chemical therapy that causes maculopathy and papillopathy when used to treat ocular tumors such as macular retinoblastoma and choroidal osteoma.

11. as an adjunct to electromagnetic radiation and steroids used to treat edema and neovascular abnormalities of the eye.

Example 6

Use of Two Different Intravitreal Brimonidine Implants to Treat Acute Rhegmatogenous Macular-Off Retinal Detachment Patients are implanted with either a 50 µg and 200 µg brimonidine posterior segment (i.e. intravitreal) implant to treat acute rhegmatogenous macular-off retinal detachment. The patients experience at least a 15-letter increase from baseline in the study eye using the Early Treatment Diabetic Retinopathy Study (ETDRS) method). The 200 µg brimonidine posterior segment implant is more effective than the 50 µg brimonidine posterior segment implant in achieving an improvement in best-corrected visual acuity (BCVA) (as measured by the proportion of patients experiencing at least a 15-letter increase from baseline in the study eye using the Early Treatment Diabetic Retinopathy Study (ETDRS) method). The 50 µg and 200 µg brimonidine posterior segment implants have acceptable safety profiles.

The patients are seen for a baseline and randomization visit on day (0), and at months 1, 3, 6, 9, 12 (masked phase) and 15, 18, and 24 months (extension phase). Additional visits on day 1 and day 7 following any re-treatments are designated as safety visits. Fifty five patients are enrolled. At least one eye of each patient has acute rhegmatogenous macular-off retinal detachment eligible for repair by scleral buckle and laser photocoagulation.

The Inclusion criteria for the patients include: eighteen years of age or older; best corrected E-ETDRS visual acuity score of >=20 letters (i.e., approximately 20/400 or better) and <=65 letters (i.e., approximately 20/50 and worse); diagnosis of acute rhegmatogenous macular-off retinal detachment in one eye. The detachment has occurred within twelve hours of presentation, and in the opinion of the investigator, can be repaired by scleral buckle placement and external laser photocoagulation of the retinal break without the anticipated need for vitrectomy or pneumatic retinopexy. The surgical repair is planned within 48 hrs of the detachment; media clarity; pupillary dilation, and; patient cooperation sufficient for adequate fundus photographs.

The study formulations are: (1) Formulation #17 of Example 1 (a solid, biodegradable rod (weighing about 1 mg implant consisted of 200 µg brimonidine tartrate and 800 µg of a poly-lactide co-polymer mixture of resomers R203 and R206 in a 1:1 weight ratio, and; (2) a solid, biodegradable rod (weighing about 1 mg implant consisted of 50 µg brimonidine tartrate and 950 µg of a poly-lactide co-polymer mixture of resomers R203 and R206 in a 1:1 weight ratio.

A significant number of the patients show an increase of 15 letters or more from baseline of BCVA using the ETDRS method at 6 months in the study eye. Hence, an intravitreal brimonidine implant can be used to treat acute rhegmatogenous macular-off retinal detachment.

Example 7

Use of Two Different Intravitreal Brimonidine Implants to Treat Chronic Retinal Injury Patients are implanted with either a 50 µg and 200 µg brimonidine posterior segment (i.e. intravitreal) implant to treat chronic retinal injury. The patients experience an improvement in best-corrected visual acuity (BCVA) (as measured by the proportion of patients experiencing at least a 15-letter increase from baseline in the study eye using the Early Treatment Diabetic Retinopathy Study (ETDRS) method). The 200 µg brimonidine posterior segment implant is more effective than the 50 µg brimonidine posterior segment implant in achieving an improvement in best-corrected visual acuity (BCVA) (as measured by the proportion of patients experiencing at least a 15-letter increase from baseline in the study eye using the Early Treatment Diabetic Retinopathy Study (ETDRS) method). The 50 µg and 200 µg brimonidine posterior segment implants have acceptable safety profiles.

The patients are seen for a baseline and randomization visit on day (0), and at months 1, 3, 6, 9, 12 (masked phase) and 15, 18, and 24 months (open label). Additional visits on day 1 and day 7 following any re-treatments are designated as safety visits. At least one eye of each patient has retinal injury at baseline of one or more of the following types: tapetoretinal degeneration, macular ischemia due to diabetic maculopathy or prior rhegmatogenous macular-off retinal detachment.

The inclusion criteria for the patients include: a least eighteen years of age; diagnosis of chronic retinal injury related to tapetoretinal degeneration, macular ischemia due to diabetic maculopathy or macular-off retinal detachment in at least one eye (the study eye); for patients with tapetoretinal degeneration the diagnosis is based on both clinical, visual field and electroretinographic findings and the visual field loss is within the central 10 degrees; for patients with macular ischemia due to diabetic maculopathy the best corrected E-ETDRS visual acuity score is >=35 letters (i.e., approximately 20/200 or better) and <=65 letters (i.e., approximately 20/50 or worse), and the decreased visual is directly related to the ischemia and not due to macular edema or previous laser photocoagulation; for patients with macular-off detachment: the macula detachment has not been present longer than 48 hours prior to repair, the repair of the detachment has occurred at least 6 months before the baseline visit, the best corrected E-ETDRS visual acuity score is >=35 letters (i.e., approximately 20/200 or better and <=65 letters (i.e., worse than approximately 20/50), the visual acuity is stable (is within one line of Snellen acuity) for at least 3 months, the repair of the detachment has been deemed an anatomic success; media clarity; pupillary dilation, and; patient cooperation sufficient for adequate fundus photographs.

The study formulations are: (1) Formulation #17 of Example 1 (a solid, biodegradable rod (weighing about 1 mg implant consisted of 200 µg brimonidine tartrate and 800 µg of a poly-lactide co-polymer mixture of resomers R203 and R206 in a 1:1 weight ratio, and; (2) a solid, biodegradable rod (weighing about 1 mg implant consisted of 50 µg brimonidine tartrate and 950 µg of a poly-lactide co-polymer mixture of resomers R203 and R206 in a 1:1 weight ratio.

A significant number of the patients show an increase of 15 letters or more from baseline of BCVA using the ETDRS method at 12 months in the study eye. Hence, an intravitreal brimonidine implant can be used to treat chronic retinal injury.

Example 8

Manufacture and In Vitro Testing of Drug Delivery Systems Containing an Alpha-2 Adrenergic Receptor Agonist and a Biodegradable Polymeric Matrix Comprising Ester End and Acid End Dolymers Introduction It is known to prepare biodegradable polymer implants capable of releasing an active agent. See for example Lewis, D., *Controlled Release of Bioactive Agents from Lactide/Glycolide Polymers* in Drugs and Pharmaceutical Sciences, Vol. 45, "Biodegradable Polymers as Drug Delivery Systems", edited by Chasin M., et al., pages 1-35 (1990), and; de Jong S., et al., *New insights into the hydrolytic degradation of poly(lactic acid): participation of the alcohol terminus*, Polymer 42 (2001); 2795-2802.

An implant (synonymously a drug delivery system) can have undesirable release characteristics. Indeed, one of the most difficult and problematic aspects of implant technology is the discovery and development of an implant with desirable and consistent active agent release characteristics. Implant release characteristics (the release profile) depends upon a multitude of factors including the chosen active agent (including it's solubility, reactivity and labiality), the selection of a particular polymer or polymers from the near infinite number of different polymers and polymer combinations available, and the manufacturing process by which the implant is made.

Undesirable implant release characteristics can include an initial burst release of the active agent and/or a lag time in the release of the active agent, both illustrated by FIG. 18. Such undesirable implant release characteristics can cause overdosing or underdosing of the patient with the active agent with resulting reduced therapeutic efficacy of the implant. Although an implant with a burst release or with a lag time may have utility in some circumstances, generally a desirable implant release characteristic is a linear rate of release of the active agent, thereby providing a constant or relatively constant dosing of the therapeutic agent to the patient.

Thus, an implant intended for intraocular administration which comprises an alpha-2 adrenergic receptor agonist (as the active agent) and a biodegradable polymeric matrix can exhibit a burst effect or a significant lag time after ocular implantation or insertion of the implant before release of a therapeutically effective amount of the alpha-2 adrenergic receptor agonist from the polymeric matrix of the implant (for example into the vitreous) takes place. A burst can be due to having too much active drug incorporated at or near the surface of an implant, and a lag time to having too little of the active agent incorporated at or near the surface of the implant. For example, for a biodegradable implant, having more than about 25% of the active agent within the polymeric matrix which comprises up to about the top 15% as measured from the exterior to the center of the implant) of the volume of the implant can result in a burst effect. Concomitantly, for a biodegradable implant, having less than about 15% of the active agent within the polymeric matrix which comprises up to about the top 25% (as measured from the exterior to the center of the implant) of the volume of the implant can result in a lag time.

Additionally, a burst effect or a lag time before release of a therapeutically effective amount of the alpha-2 adrenergic receptor agonist from the polymeric matrix of the implant (for example into the vitreous) can be due to a selection of polymer or polymers for constituting the polymeric matrix of the implant which polymer or polymers have characteristics which do not permit the active agent to be released with a linear or substantially linear release profile. Although broad or general polymer characteristics are known (see example Lewis (1990) and de Jong S. (2001) supra) there is a near infinite variety of different polymer or polymer combinations (each with their own degradation rates, pore forming characteristics, reactivities, degradation pathways, intermediates, by products, active agent-polymer association characteristics, etc) which can be used to constitute the polymeric matrix of the implant.

The size and weight of implants intended for intraocular administration is significantly limited by the dimensions of intraocular spaces and potential intraocular spaces. Additionally, even when it may be physically possible to insert, implant or inject an implant to or into a particular intraocular site, considerations such as a desire to reduce injury to sensitive ocular tissues at the site of and adjacent to the site of administration site, and to not interfere with vision can require the implant to be less than it's maximum pp size and weight. Ocular tissue injury can result in inflammation, pain, increased healing time and reduced visual acuity. In light of these considerations, an implant intended for example for intravitreal administration preferably has no dimension greater than about 20 mm and weighs less than about 5 mg. For our purposes, the weight of the implant is the weight of the active agent incorporated into the implant plus the weight of the polymers or polymers which comprise the polymeric matrix of the implant. Having too little of the active agent incorporated into the implant can result in having too little implant surface active agent (that is having only a minute absolute weight amount of the active agent present within a few microns of the exterior surface of the implant). Implant surface active agent is available for immediate or rapid (i.e. within the first day or two after implantation) release from the polymeric matrix. Additionally, having a low amount of implant surface soluble active agent can delay implant surface pore formation which thereby slows the release of the active agent from deeper within the implant. To address this problem pore forming additives have been used to improve the initial release of an active agent from a biodegradable implant, but unfortunately use of pore forming additives can result in a significant decrease in the duration of the time over which a therapeutically effective amount of the active agent is released from the implant.

Summary

With an awareness of these problems and deficiencies of prior implants and in light of the considerations above, we have developed implants intended for the treatment of ocular conditions comprising an alpha-2 adrenergic receptor agonist (as the active agent) and a biodegradable polymeric matrix with the following desirable characteristics:

1. No burst effect and as well no or a nominal lag time after ocular implantation or insertion of the implant before release of a therapeutically effective amount of the alpha-2 adrenergic receptor agonist from the implant occurs. Generally, we found that a suitable initial release of the active agent from the implant as well as a long-term sustained release of the active agent from the implant could be achieved by particular novel selections of hydrophobic poly (D,L,-lactide) polymers and/or hydrophilic poly(D,L,-lactide-co-glycolide) polymers to comprise the polymeric matrix of the implant.

2. high dose implants, that is implants which comprise more than 4 weight percent (wt %) of a biologically active alpha-2 adrenergic receptor agonist. The remaining 96 wt % or less of the implant will typically comprise one or more biocompatible and biodegradable polymers.

3. absence of pore forming additives or other release rate modulators or modifiers.

4. sustained release of a therapeutic amount of an alpha-2 adrenergic receptor agonist from the biodegradable polymeric matrix over a period of at least 115 days (about 4 months).

5. substantially linear (i.e. first order release rate kinetics) release of an alpha-2 adrenergic receptor agonist from the biodegradable polymeric matrix of the implant over a period of time of from about 20 days to about 50 days. "Substantially linear release" means that the measured amount of the rate of alpha-2 adrenergic receptor agonist release from the biodegradable polymeric matrix of the implant does not vary by more than 50% over a three day period, preferably does not vary by more than 30% over a seven day period and most preferably does not vary by more than 20% over a ten day period.

Thus, we made brimonidine tartrate containing sustained release polymer implants with exhibited desirable in vitro release profile of the brimonidine tartrate[1]. Generally the release profiles showed no or a reduced initial drug burst and as well sustained release profile of the active agent over a period of at least about 115 days. Our novel implant formulations contained hydrophobic ester end-capped poly(D,L-lactide) homopolymers, ester end-capped poly(lactide-co-glycolide) copolymers, and a minor amount of acid end-capped poly(D,L,-lactide-co-glycolide) polymer. An uncapped polymer (such as a PLGA polymer) has a free carboxyl group at the polymer terminus. Without wishing to be bound by theory we believe that these desirable implant release characteristics were obtained because the polylactide component of the polymers used can provide an implant polymeric matrix with a relatively long hydrolysis half-life as well as a durable polymeric matrix capable of retaining the active agent within the implant polymer matrix for an extended period of time. Additionally, the acid-end capped lactide-glycolide polymer can act to speed initial active agent drug release from the implant by enhancing early water penetration into the implant by raising the surface energy of the implant. The acid-end capped lactide-glycolide polymer can also create a more porous implant as it swells and is eroded from the implant because its hydrolysis rate is much faster than that of the polylactide.

[1] Brimonidine tartrate is a relatively selective alpha-2 adrenergic agonist approved for ophthalmic use. The chemical name of brimonidine tartrate is 5-bromo-6-(2-imidazolidinylideneamino) quinoxaline L-tartrate. It is an off-white, pale yellow to pale pink powder. In solution, brimonidine tartrate has a clear, greenish-yellow color. Brimonidine tartrate has a molecular weight of 442.24 as the tartrate salt and is water soluble (34 mg/ml). The molecular formula is $C_{11}H_{10}BrN_5 \cdot C_4H_6O_6$.

Experiments

We carried out experiments to make and to test our particular drug delivery systems comprising an alpha-2 adrenergic receptor agonist and a biodegradable polymeric matrix comprising both ester end capped and acid end capped polymers. In particular we made and tested in vitro brimonidine tartrate containing sustained release polymer implants intended for intravitreal administration to treat an ocular condition.

Examples of three implants formulation we made comprising an alpha-2 adrenergic receptor agonist and a biodegradable polymeric matrix are shown in Table 4. The in vitro release rates of the three Table 4 implants over a 21 day period (in phosphate buffered saline ("PBS") at pH 7.4 and 370° C. is shown by FIG. 19.

As shown in Table 4 and in FIG. 19, a particularly advantageous implant formulation made was formulation number 7746-073. Implant formulation 7746-073 comprised 12 wt % brimonidine tartrate, 53 wt % R203S (an ester end-capped poly(D,L,-lactide) polymer), 25 wt % R208 (also an ester end-capped poly (D,L,-lactide) polymer), and 10% RG502H (an acid end-capped poly(D,L-lactide-co-glycolide) polymer). Resomers RG502H, R208 and R203S can be obtained from Boehringer Ingelheim. RG502H comprises 48-52 mol % D,L-lactide and 48-52 mol % glycolide (as determined by NMR spectroscopy) and has an inherent viscosity at 25° C. of 0.16 to 0.24 dl/g. R208 has an inherent viscosity at 25° C. of 1.8 to 2.2 dl/g. R203S has an inherent viscosity at 25° C. of 0.25 to 0.35 dl/g.

TABLE 4

Formulations of Three Brimonidine Tartrate Implants

| Formulation No | w/w, % | | | |
|---|---|---|---|---|
| | Brimonidine Tartrate | Resomer R203S | Resomer R208 | Resomer RG502H |
| 7746-073 | 12 | 53 | 25 | 10 |
| 7702-020 | 15 | 60 | 25 | 0 |
| 7702-022 | 18 | 65 | 17 | 0 |

As shown by FIG. 19, in distinction to the implant formulations which contained only ester end-capped biodegradable polymers (formulations 7702-020 and 7702-022), the implant formulation which contained a mixture of ester end-capped and acid end-capped polymers (formulation 7746-073) showed an essentially linear rate of release of the brimonidine tartrate active agent in vitro over the two week period of days 7-21.

Additionally, as shown by FIG. 20, when the release of the active agent from formulation 7746-073 was observed over a longer period of time (in PBS at pH 7.4 and 37° C.), linear rates of release of the brimonidine tartrate active agent in vitro were observed during the time periods from about day 30 to about day 45 (15 day period), from about day 50 to about day 90 (40 day period) and from about day 100 to about day 115 (15 day period).

We then made seven additional implant formulations each comprising an alpha-2 adrenergic receptor agonist and various ratios of ester end-capped and acid-end capped biodegradable polymers as shown in Table 5. In Table 5 R203S and R208 are ester end-capped poly(D,L,-lactide) polymer resomer supplied by Boehringer-Ingelheim (Resomer), RG502H is an acid end-capped poly(D,L-lactide-co-glycolide) polymer and RG752 is another ester end capped poly (D,L,-lactide-co-glycolide) polymer. APO40 is an ester end-capped poly (D,L,-lactide) polymer with an inherent viscosity at 30° C. of 0.34-0.40 dl/g, available from Durect Corporation (Lactel). All inherent viscosities for all resomers set forth herein were measured using $CHCl_3$ as solvent.

The in vitro release rates of the seven Table 5 implant formulations over a 14-26 day period (in PBS at pH 7.4 and 37° C.) is shown by FIG. 21. Significantly, FIG. 20 shows linear release profiles of the Table 5 Formulations, all of which contained acid end-capped polymer in combination with poly(D,L,-lactide) and poly(lactide-co-glycolide) polymers.

Thus, FIG. 21 shows that a linear release profile of the active agent can be obtained with different combinations of ester end-capped and acid end-capped polymers, even when: (1) the active agent loading in the polymeric matrix is varied between about 9 wt % and about 12 wt %, and; (2) the wt % of acid end-capped polymer compositions is varied from about 15 wt % to about 35 wt %, the remainder of the implant being a combination of two or three different ester end-capped polymers.

TABLE 5

Linear Release Brimonidine Tartrate Containing Formulations

| FormulationNo | w/w, % | | | | | |
|---|---|---|---|---|---|---|
| | Brimonidine Tartrate | APO40 | Resomer R203S | Resomer R208 | Resomer RG502H | Resomer RG752 |
| 7746-061A | 12 | 25 | 0 | 25 | 15 | 23 |
| 7702-068A | 10.9 | 31.8 | 0 | 22.7 | 16.4 | 18.2 |
| 7702-065A | 12 | 35 | 0 | 35 | 18 | 0 |
| 7702-070A | 12 | 25 | 0 | 25 | 18 | 20 |
| 7702-058A | 12 | 23 | 0 | 40 | 25 | 0 |
| 7702-62A | 12 | 20 | 0 | 20 | 25 | 23 |
| 7702-054A | 9 | 0 | 6 | 50 | 35 | 0 |

The polymeric implants in this study were made by melt extrusion in a Daca instruments microcompounder/extruder, but they can also be made by direct compression. The implants made were rod-shaped, but they can be made into any geometric shape by changing the extrusion or compression die.

Polymers were used as received from Boehringer Ingelheim (Resomer) or Durect (APO40) and the brimonidine tartrate was used as the salt. The polymers and brimonidine tartrate were combined in a Retsch ball-mill capsule with a ¼" stainless steel ball; then the capsule was placed in the Retsch mill (Type MM200) for 5 min at 20-cycles/min. The capsule was removed from the mill and the powder blend was stirred with a spatula. The capsule with the powder blend was mixed for 5 minutes on a Turbula mixer. The powder blend is inspected for homogeneity and the mixing procedure is repeated if necessary.

The Daca microcompounder/extruder was setup according to the manufacture's instructions. The output of the Daca is fitted with a laser micrometer and a custom built puller to control the diameter of the extruded rod. The Daca was allowed to equilibrate to the extrusion temperature; then the powder blend was manually fed into the extrusion screws at a rate that maintained a constant load and torque. All the Example 8 and Example 9 implant filaments were made at extrusion temperatures between 95° C. and 115° C. The filaments made were cut into one-milligram rods approximately 6 mm long and each with a diameter of about 0.018 (about 0.46 mm). Extruded filament active agent release was monitored by HPLC in phosphate buffered saline pH 7.4 at 37° C.

Example 9

Manufacture and In Vitro Testing of Drug Delivery Systems Containing Two Forms of an Alpha-2 Adrenergic Receptor Agonist and an Ester End-Capped Biodegradable Polymeric Matrix In Example 1 above filament shaped implants containing brimonidine free base and brimonidine tartrate were made using the single polymer resomers R203, R206 or RG752. See Formulations 11-15 and 19-20 in Table 1. These Example 1 implants were made using a process with mixing, melting, pelletizing and melt extrusion steps.

In this Example 9 experiment we made implants containing brimonidine free base and brimonidine tartrate using a combination of two different polymer resomers and a different and improved manufacturing process, as compared to Example 1. The Example 9 sustained release implants having improved release profiles were made using the Example 8 process, that is by combining a brimonidine free base and a brimonidine tartrate followed by stirring, mixing, and melt extrusion of implant filaments. The filaments made were cut into one-milligram rods, approximately 6 mm long and each with a diameter of about 0.018 (about 0.46 mm).

In this Example 9, the polymer matrix consisted of two poly(D,L-lactide) PLA polymers, although many different types of polymers can be used. The improvement in the release kinetics is primarily a function of the physicochemical properties of the brimonidine free base and the brimonidine tartrate. Therefore the substantially linear active agent release kinetics can be obtained with a variety of other polymers, beyond the two poly(D,L-lactide) PLA polymers used in this experiment. Because brimonidine tartrate is more water soluble than is brimonidine free base, implants made with the tartrate can show a burst release due to the availability of implant surface brimonidine tartrate. On the other hand, brimonidine free base is not water soluble, thereby making the implant more hydrophobic and delaying initial water permeation into the implant and consequently therefore also the release of brimonidine, resulting in an observed lag before a therapeutic amount of the brimonidine free base is released from the implant.

Based on the known solubility difference between brimonidine free base and a brimonidine tartrate, the expected release rate of brimonidine from an implant which comprises both brimonidine free base and a brimonidine tartrate would be proportional to the amount of brimonidine tartrate in the formulation. Surprisingly, we discovered that an implant which comprises a combination of a brimonidine free base and a brimonidine tartrate has a synergistic release profile, that is the release of brimonidine from the combination implant is faster than the release rate of brimonidine from an implant which comprises only a brimonidine tartrate, with no brimonidine free base. FIG. 22 (in vitro release in PBS at pH 7.4 and 37° C.) shows that an implant which comprises a combination of the two forms (brimonidine free base and brimonidine tartrate) shows a faster release than for either individual form of brimonidine in an implant by itself.

An embodiment of our new formulation can comprise brimonidine free base, brimonidine tartrate, and a biodegradable polymer, such as a hydrophobic biodegradable polymer. The hydrophobic biodegradable polymer can be an ester end-capped polymer. The hydrophobic biodegradable polymer can be an ester end-capped polymer, such as a hydrophobic, ester end-capped poly(D, L-lactide) homopolymer. Another embodiment of our invention can comprise two hydrophobic, ester end-capped poly(D, L-lactide) homopolymers, as shown by the six Table 6 formulations. The polylactides can have a relatively long hydrolysis half life and can provide a more durable matrix to retain the active agent within the implant for an extended period.

As shown by FIG. 22 our implant formulation 7746-146 which comprised 17.5% brimonidine free base, 17.5% brimonidine tartrate, 40% of the ester end-capped poly(D,L,-lactide) polymer R203S, and 25% of the ester end-capped poly (D,L,-lactide) polymer R208 had a release profile which was faster than the formulations which contained only a brimonidine free base or only a brimonidine tartrate (formulations 7746-118, 7746-141, 7746-092A and 7746-142 in Table 5). Significantly, the 7746-146 formulation had a first 20 day linear release profile followed by a second, different 40 day linear release profile. Notably, formulation 7746-147 which also comprised a combination of brimonidine free base and brimonidine tartrate, showed an analogous active agent release profile but with a different polymer ratio. All the formulations are summarized in Table 6.

TABLE 6

Brimonidine Tartrate Containing Formulations

| | w/w, % | | | |
| --- | --- | --- | --- | --- |
| Formulation No | Brimonidine Free Base | Brimonidine Tartrate | Resomer R203S | Resomer R208 |
| 7746-146 | 17.5 | 17.5 | 40 | 25 |
| 7746-118 | 0 | 35 | 40 | 25 |
| 7746-141 | 35 | 0 | 40 | 25 |
| 7746-147 | 17.5 | 17.5 | 55 | 10 |
| 7746-092A | 0 | 35 | 55 | 10 |
| 7746-142 | 35 | 0 | 55 | 10 |

Example 10

Treatment of Elevated Intraocular Pressure with an Intravitreal Biodegradable Polymeric, Brimonidine Containing Implant In Example 2 above it was disclosed that surgical placement into the vitreous of normotensive monkey eyes of a brimonidine containing biodegradable polymeric implant did not lower IOP in the monkeys as compared to placebo. See eg FIG. 12.

In this Example 10 we surprisingly show that surgical placement into the vitreous of hypertensive monkey eyes of a brimonidine containing biodegradable polymeric implant does lower IOP in the monkeys as hypertensive compared to placebo hypertensive monkey eyes. See eg FIG. 23. Example 10 can therefore be viewed as a further rendition of, supplement or extension of Example 3.

In this experiment we observed the effect on intraocular pressure (IOP) of brimonidine containing drug delivery system inserted into the vitreous of rabbit eyes (Dutch Belted rabbits). Elevated IOP was induced in the rabbits by intracameral injection of Carbopol 934P, an ocular hypertensive (OHT) drug. IOP was measured using a hand held pneumatonometer.

Just as in Example 2, the extruded rod shaped Formulation 17 implant of Example 1 was used as the brimonidine containing implant in this Example 10 experiment. Thus, the active agent implant used weighed about 1 mg and comprised 20 wt % brimonidine tartrate (200 µg), 40 wt % resomer R203, and 40 wt % resomer R206 (800 µg polylactide polymer). The Formulation 17 placebo 1 mg implant used comprised 50 wt % resomer R203 and 50 wt % resomer R206 (1 mg polylactide polymer).

An implant was placed in the right eye only of twelve Dutch Belted rabbits as follows. The rabbits were sedated by intravenous syringe injection of Ketamine given in a dose of 15 mg per kg of rabbit weight (mg/kg) combined with acepromazine maleate 1 mg/kg. Next 1-2 drops of ocular Betadine was applied to the right eye as a topical disinfectant followed by 1-2 drops of Proparacaine applied to the right eye as a topical anesthetic.

The brimonidine containing implant was placed in the vitreous of six right eyes and the placebo implant was placed in the vitreous of the other six eyes. The implants were placed by making an incision 4 mm from the limbus into the vitreous. In six right eyes an extruded rod brimonidine implant was so placed. After implantation topical antibiotic ointment was applied to each right eye.

On the day after implantation, ocular hypertension was induced as follows. The rabbits were sedated with sedated by intravenous syringe injection of Ketamine 15 mg/kg combined with acepromazine maleate 1 mg/kg. Next 1-2 drops of ocular Betadine was applied to the right eye as a topical disinfectant followed by 1-2 drops of Proparacaine applied to the right eye as a topical anesthetic. Next 50 µl of 0.3% Carbopol 934P solution at pH 4 was administered to each right eye by intracameral injection, followed by application of topical antibiotic ointment to the right eye.

Figure 23:
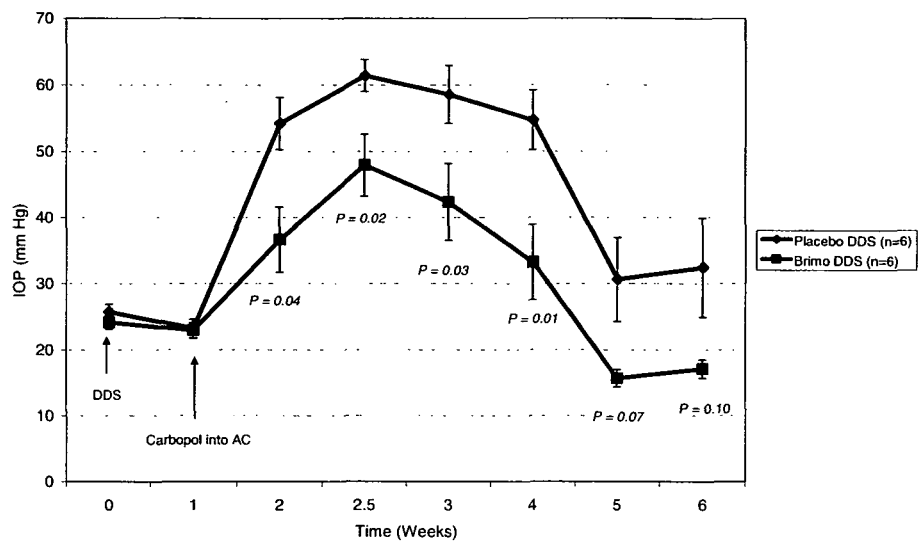
FIG. 23 is a graph showing intraocular pressure (in mm Hg) on the Y-axis and time in weeks on the X-axis after intravitreal placement of the Example 10 brimonidine implant in hypertensive rabbit eyes.

As shown by FIG. 23, as compared to placebo the brimonidine containing implant lowered IOP in the hypertensive right eyes of the subject rabbits for up to six weeks after DDS implantation.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

We claim:

1. A method of treating a symptom of glaucoma, the method comprising the step of placing into the vitreous of an eye a melt extruded, monolithic, biodegradable intraocular implant comprising brimonidine tartrate associated with a biodegradable polymer, wherein the biodegradable polymer comprises a mixture of:
    a) an ester end-capped biodegradable poly(D,L-lactide) homopolymer having an inherent viscosity at 25° C. in 0.1% $CHCl_3$ of 0.25 to 0.35 dl/g;
    b) an ester end-capped biodegradable poly(D,L-lactide) homopolymer having an inherent viscosity at 25° C. in 0.1% $CHCl_3$ of 1.8 to 2.2 dl/g; and
    c) an acid end-capped biodegradable poly(D,L-lactide-co-glycolide) copolymer comprising 48-52 mol % D,L-lactide and 48-52 mol % glycolide and having an inherent viscosity at 25° C. in 0.1% $CHCl_3$ of 0.16 to 0.24 dl/g.

2. The method of claim 1, wherein the biodegradable intraocular implant comprises:
    a) 12 weight percent of said brimonidine tartrate;
    b) 53 weight percent of said ester end-capped biodegradable poly(D,L-lactide) homopolymer having an inherent viscosity at 25° C. in 0.1% $CHCl_3$ of 0.25 to 0.35 dl/g;
    c) 25 weight percent of said ester end-capped biodegradable poly(D,L-lactide) homopolymer having an inherent viscosity at 25° C. in 0.1% $CHCl_3$ of 1.8 to 2.2 dl/g; and
    d) 10 weight percent of said acid end-capped biodegradable poly(D,L-lactide-co-glycolide) copolymer having an inherent viscosity at 25° C. in 0.1% $CHCl_3$ of 0.16 to 0.24 dl/g.

3. The method of claim 1, wherein the symptom of the glaucoma is elevated intraocular pressure.

4. A method for treating macular degeneration, the method comprising the step of intraocular administration of a melt extruded, monolithic, biodegradable intraocular implant comprising brimonidine tartrate associated with a biodegradable polymer, wherein the biodegradable polymer comprises a mixture of:
    a) an ester end-capped biodegradable poly(D,L-lactide) homopolymer having an inherent viscosity at 25° C. in 0.1% $CHCl_3$ of 0.25 to 0.35 dl/g;
    b) an ester end-capped biodegradable poly(D,L-lactide) homopolymer having an inherent viscosity at 25° C. in 0.1% $CHCl_3$ of 1.8 to 2.2 dl/g; and
    c) an acid end-capped biodegradable poly(D,L-lactide-co-glycolide) copolymer comprising 48-52 mol % D,L-lactide and 48-52 mol % glycolide and having an inherent viscosity at 25° C. in 0.1% $CHCl_3$ of 0.16 to 0.24 dl/g.

* * * * *